(12) United States Patent
McCormick

(10) Patent No.: US 12,727,872 B2
(45) Date of Patent: Sep. 8, 2026

(54) DEVICES AND METHODS FOR SURGICAL SUTURING

(71) Applicant: Davol Inc., Warwick, RI (US)

(72) Inventor: Daniel F. McCormick, Bolton, MA (US)

(73) Assignee: Davol Inc., Warwick, RI (US)

( * ) Notice: Subject to any disclaimer, the term of this patent is extended or adjusted under 35 U.S.C. 154(b) by 153 days.

(21) Appl. No.: 18/289,183

(22) PCT Filed: May 5, 2022

(86) PCT No.: PCT/US2022/027877

§ 371 (c)(1),
(2) Date: Nov. 1, 2023

(87) PCT Pub. No.: WO2022/235937

PCT Pub. Date: Nov. 10, 2022

(65) Prior Publication Data

US 2024/0215970 A1 Jul. 4, 2024

Related U.S. Application Data

(60) Provisional application No. 63/185,668, filed on May 7, 2021.

(51) Int. Cl.
*A61B 17/04* (2006.01)

(52) U.S. Cl.
CPC .. *A61B 17/0401* (2013.01); *A61B 2017/0406* (2013.01); *A61B 2017/0414* (2013.01); *A61B 2017/0464* (2013.01)

(58) Field of Classification Search
CPC ............ A61F 2/0063; A61F 2210/0004; A61F 2220/0075; A61F 2/08; A61F 2/0811;
(Continued)

(56) References Cited

U.S. PATENT DOCUMENTS

| | | | |
|---|---|---|---|
| 5,527,341 | A | 6/1996 | Gogolewski et al. |
| 6,712,830 | B2 | 3/2004 | Esplin |

(Continued)

FOREIGN PATENT DOCUMENTS

| | | | |
|---|---|---|---|
| JP | H06-14946 | A | 1/1994 |
| JP | 2017-533803 | A | 11/2017 |

(Continued)

OTHER PUBLICATIONS

Extended European Search Report mailed Jan. 24, 2025 for European Application No. 22799598.2.

(Continued)

*Primary Examiner* — Katherine M Shi

(57) ABSTRACT

Surgical devices and related methods for use with sutures are generally described. In some embodiments, a surgical device may include an elongated body and a plurality of through holes configured to allow a suture to pass through the plate across opposing edges of a defect site. The plate may shield neighboring tissue from tension in the suture line by redistributing the tension along its body. In some embodiments, the disclosed surgical devices may reduce the likelihood of defect closure failure caused by the suture pulling through a tissue defect. In some embodiments, the through holes may be located on offset parallel axes to reduce excessive suture friction and suture mismanagement. The disclosed surgical devices may be used with either interrupted or continuous suture patterns.

16 Claims, 16 Drawing Sheets

(58) Field of Classification Search

CPC .......... A61B 17/0401; A61B 17/00234; A61B 2017/0464; A61B 17/0466; A61B 2017/0404; A61B 2017/0406

See application file for complete search history.

(56) References Cited

U.S. PATENT DOCUMENTS

| | | | | |
|---|---|---|---|---|
| 2004/0254609 | A1* | 12/2004 | Esplin .................. | A61F 2/0811 606/232 |
| 2006/0029633 | A1 | 2/2006 | Kaiser et al. | |
| 2014/0243859 | A1 | 8/2014 | Robinson | |
| 2016/0120631 | A1 | 5/2016 | Murphy | |

FOREIGN PATENT DOCUMENTS

| | | | |
|---|---|---|---|
| KR | 10-2019-0100583 | A | 8/2019 |
| WO | WO 2014/100109 | A1 | 6/2014 |
| WO | WO 2021/032778 | A1 | 2/2021 |

OTHER PUBLICATIONS

International Search Report and Written Opinion mailed Sep. 6, 2022 for International Application No. PCT/US2022/027877.

International Preliminary Report on Patentability mailed Nov. 16, 2023 for International Application No. PCT/US2022/027877.

* cited by examiner

DEVICES AND METHODS FOR SURGICAL SUTURING

CROSS-REFERENCE TO RELATED APPLICATIONS

This application is a national stage filing under 35 U.S.C. § 371 of International Patent Application Serial No. PCT/US2022/027877, filed May 5, 2022, which claims priority to U.S. Application Ser. No. 63/185,668, filed May 7, 2021, the disclosures of each of which are incorporated herein by reference in their entirety.

FIELD

The technology is generally related to surgical devices and related methods. More specifically, devices and methods for surgical suturing are disclosed.

BACKGROUND

Existing surgical methods make use of tensioned suture lines to close a defect (e.g., a wound) or attach an implant or prosthetic to preexisting tissue. In instances where the defect is formed in soft tissue, a suture may pull through the tissue given the tensile forces along the suture line, especially when the suture is tightened to close the defect. Such pull-through events may not only prevent defect closure but may undesirably introduce new defects to the tissue (e.g., tear sites along a wound edge).

An operator (e.g., a surgeon) may employ various suture pattern types to suitably close a defect. Interrupted sutures are typically easy to place and individually controllable (both in position and tension), which may allow the suture path to follow a convoluted defect interface, but are more time consuming to place and tighten. In contrast, continuous sutures are typically faster to place and remove than interrupted sutures and typically use less suture material, but are more difficult to tighten uniformly along the interface of a tissue defect.

SUMMARY

In some embodiments, a surgical device for securing sutures to soft tissues includes an elongated body with a length and a width, a first plurality of through holes, and a second plurality of through holes. The length of the elongated body is greater than the width of the elongated body. The first plurality of through holes extend from a first surface of the elongated body to a second surface of the elongated body opposite from the first surface. The first plurality of through holes are positioned along at least a first portion of the length of the elongated body. The second plurality of through holes extend from the first surface of the elongated body to the second surface of the elongated body opposite from the first surface. The second plurality of through holes are positioned along at least a second portion of the length of the elongated body. The second plurality of through holes is offset from the first plurality of through holes in a transverse direction parallel to the width of the elongated body.

In some embodiments, a method of securing sutures to soft tissue includes passing a first end of a suture from a first side of a defect through a first through hole of a first plurality of through holes of a surgical device and passing a second end of the suture from an opposing side of the defect through a first through hole of a second plurality of through holes of the surgical device. The first plurality of through holes are positioned along at least a first portion of a length of the surgical device, and the first plurality of through holes extend from a first surface of the surgical device to a second surface of the surgical device. The second plurality of through holes are positioned along at least a second portion of the length of the surgical device, and the second plurality of through holes extend from the first surface of the surgical device to the second surface of the surgical device. The second plurality of through holes is offset from the first plurality of through holes in a transverse direction parallel to a width of the surgical device It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying FIGURES.

BRIEF DESCRIPTION OF DRAWINGS

The accompanying drawings are not intended to be drawn to scale. In the drawings, each identical or nearly identical component that is illustrated in various FIGURES may be represented by a like numeral. For purposes of clarity, not every component may be labeled in every drawing. In the drawings.

DETAILED DESCRIPTION

Figure 1:
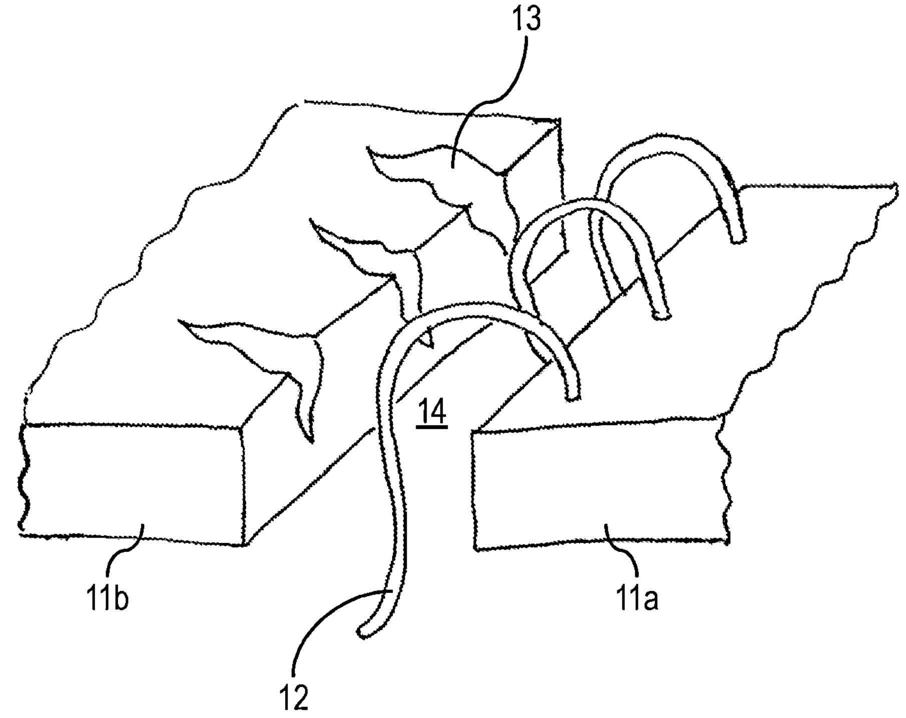
FIG. 1 is a schematic view of a series of sutures after tearing through a tissue defect.

Tensioned suture lines are a surgical standard for soft tissue defect closure. The advent of minimally or non-invasive surgical procedures has encouraged such defect closure procedures to take place robotically. However, due to the lack of tactile feedback from the robotic instrument to the operator, the Inventors have recognized that the operator (e.g., surgeon) may be less able to determine a maximum tensile stress applied along the suture line which may result in increased likelihood of suture pull-through. As described previously, suture pull-through may cause defect closure failure and other undesirable consequences.

In some instances, a buttressing pledget with through holes formed therein for receiving sutures may be used to reduce the risk of suture pull-through in surgical applications. The pledget may be placed along a suture line to prevent approximation of the suture line across a defect (which can occur during suture pull-through) by shielding underlying soft tissue from tension in the suture line. However, the Inventors have recognized that suture lines in existing buttressing pledgets suffer from excessive frictional drag along neighboring suture lines, which can lead to suture breakage. Additionally, when these pledgets are used with complex suture patterns, the Inventors have recognized that the suture lines may become convoluted, which may lead to suture mismanagement, suture breakage, and/or improper defect closure.

In view of the above, the Inventors have recognized the benefits associated with buttressing pledgets which make sure of through holes distributed along staggered parallel lines. For example, in some embodiments a buttressing pledget (also referred to herein as a "device") may include two or more groups of through holes extending at least partially along a length of the device. The groups of through holes may be offset from one another. Accordingly, sutures may be passed through the two or more groups of through holes in a desired suturing pattern to close an associated tissue defect. The offset through holes may physically separate suture ends and reduce contact between suture lines prior to defect closure. In other words, the offset through holes may reduce suture interference (and subsequent friction generation and/or suture breakage) by separating suture lines extending from opposing edges of a defect. Specific arrangements of the through holes and corresponding suture patterns that may be used with the various devices disclosed herein are elaborated on below.

In some embodiments, a device may include an elongated body with a plurality of through holes distributed along the body. The through holes may be configured to accommodate a suture line that passes from one edge of a defect to another opposing edge of the defect. The distribution of the through holes may be determined by the defect size, appropriate bite size (measured from a defect edge to a puncture point of the needle or any other instrument used to deploy the suture line), suture pattern, suture size, and any other number of factors which an operator (e.g., a surgeon) may consider. The elongated body may be configured to lay across a defect, along a defect, or may be oriented in any direction with respect to the defect edges in order to aid in closing the tissue defect during use.

According to some embodiments, the through holes may be arranged with respect to a specific suture pattern. As described above, the operator may employ different suture patterns in response to a variety of factors corresponding to a particular defect closure site. The suture pattern may be an interrupted, continuous, appositional, inverting, everting, tension, or any other class of suture patterns. In some embodiments, the device may be used with a pulley stitch pattern. The device may also be used with interrupted and continuous simple sutures (sometimes known as "over-and-over"), interrupted and continuous subcuticular, interrupted and continuous horizontal mattress, interrupted and continuous vertical mattress, interrupted and continuous Lembert, Cushing, lock-stitch, Halsted, Connell, purse-string, alpha, zigzag, coil, switch-back, finger-trap, Gambee, cruciate suture patterns, Ford-interlocking, Parker-Kerr, far-far-near-near, far-near-near-far, near-far-far-near, interlocking loop, three loop pulley, or any other suitable suture pattern.

The devices described herein may be used in any suitable surgical or non-surgical application. For example, the device may be used as a buttressing pledget for fascial defect closure procedures in hernia repairs. The device may also be used for other tissue defect closure and/or implant attachment procedures such as appendectomies, biopsies, carotid endarterectomies, cataract repairs, Cesarean section, cholecystectomies, cardiac bypass, debridement (of wounds, burns, infections, etc.), tissue grafts, tonsillectomies, or any other suitable surgical procedure. The device may be used in defect closure for soft tissue, cartilage, ligament, bone, or any other biological material. It should be appreciated that the current disclosure is not limited by application or type of defect it is used for.

It should be appreciated that a surgical device may formed of any material or combinations of materials. In some embodiments, the device may be formed of a material which is stiffer than the material in which the defect is formed. For example, the device may be formed of a material which is stiffer and/or has a greater resistance to tearing as compared to soft tissue. In this way, the device may provide greater resistance against tear-through than the material it is used to close. In surgical applications, the device may be formed of a biocompatible material, whereas in non-surgical applications, the device may be formed of any desired material including non-biocompatible material. In some embodiments, the device may be formed of a flexible material, such as foam, felt, or fabric. Though embodiments in which a rigid plastic and/or metal are used to form a device are also contemplated. The device may also be formed of a material capable of absorbing fluid from the approximated material (e.g., blood from a defect) and/or may have hemostatic properties. Accordingly, the device may minimize the leakage of fluids from either the original defect site, or fluids which may leak due to penetration of tissue by a suture needle or suture.

In some embodiments, a device as disclosed herein may be configured to remain at the defect site as an implanted device and may not significantly degrade over time. The operator may choose to remove the device during a suture removal procedure or may leave the device within, or on, the body depending on if the closure procedure is an external or internal closure procedure. In other embodiments, the device may be made from a biodegradable and/or bioresorbable material such that the device degrades over a given period of time due to exposure to physiological temperature, hydration, enzyme presence, and/or any other degradability factor. In view of the above, a device may be formed of any appropriate biocompatible, non-biocompatible, non-bioresorbable material, a bioresorbable material, combinations of the forgoing, and/or any other appropriate type of material as the disclosure is not limited in this fashion. In some specific embodiments, a device may be formed of polyurethane, polyamide, polyethylene, polypropylene, polyethylene terephthalate, polyvinyl chloride, polyolefin, polycarbonate, polycarbamate, polyacrylate, polystyrene, polyurea, polyether, polyalkylether, polyamine, polytetrafluoroethylene, polylactic acid, polyglycolic acid, poly(lactic-co-glycolic acid), poly(glycolide-co-trimethylene carbonate), polydioxanone, polycaprolactone, polyhydroxybutyrate, poly(phosphazenes), poly(D,L-lactide-co-caprolactone), poly(glycolide-co-caprolactone), poly(phosphatase ester), polyanhydrides, polyesters, polyphosphazenes, polyacrylates, polymethacrylates, co-polymers, block polymer, block co-polymers, linear polymer, branched polymer, dendritic polymer, cross-linked polymer, metals (e.g., stainless steel, titanium), any combination thereof, or any other suitable material, as the present disclosure is not so limited. In some embodiments, the device may be formed of a natural material, such as autologous tissue, natural polymers such as polysaccharides (e.g., cellulose), proteins, or any other natural material. In some embodiments, the device may be formed of a composite material, such as a fiber-reinforced material.

As used herein, the term "bioresorbable." "degradable," or other similar term may refer to a material which is bioresorbable, absorbable, and/or degradable in response to physical or chemical cues within physiological environments or any other environment in which the device is used. For example, a bioresorbable material may be eliminated from a physiological environment over a given period of time due to chemical interactions with the enzymes, temperature, pH, or any other chemical marker.

In embodiments where the device is formed of at least one bioresorbable material, the material may degrade in vivo after the defect has healed. The device may degrade in vivo after 2 days, 4 days, 5 days, 1 week, 2 weeks, 3 weeks, 1 month, 1.5 months, 2 months, 3 months, or any other suitable duration of time.

The surgical devices described herein are not limited by the material composition or the types of suture that may be used with the device. For example, a suture may be formed of a natural or synthetic material. In some embodiments, the suture may be formed of a softer material than the device and/or have an appropriate cross-section, such that the suture may not pull through the device or damage the device prior to reaching a breaking load of the suture. The suture may be formed of a non-bioresorbable material, such as polypropylene, polycarbonate, nylon, polyester, polyamide, polypropylene, poly(ethylene terephthalate), stainless steel, titanium, any combinations thereof, or any other suitable non-bioresorbable material. In some embodiments, the suture may be formed of a bioresorbable material, such as polydioxanone, polylactic acid, polyglycolic acid, poly(lactic-co-glycolic acid), biomaterials (e.g., collagen, cellulose), any combination thereof, or any other suitable material.

In embodiments where both the suture and the device are formed of a bioresorbable material, the suture and the device may degrade in vivo during the same period of time. In other embodiments, the device may degrade faster than the suture. In other embodiments still, the suture may degrade faster than the device. In some embodiments, a bioresorbable suture line may be used with a non-bioresorbable device. In other embodiments, a non-bioresorbable suture line may be used with a bioresorbable device. In other embodiments still, a non-bioresorbable suture line may be used with a non-bioresorbable device. It should be appreciated that the present disclosure is not limited by the material composition or degradability properties of the suture or the device.

Turning to the FIGURES, specific non-limiting embodiments are described in further detail. It should be understood that the various systems, components, features, and methods described relative to these embodiments may be used either individually and/or in any desired combination as the disclosure is not limited to only the specific embodiments described herein. For example, while all the embodiments described herein refer to surgical devices used to approximate soft tissue, the device described herein may be configured to be used in any application wherein soft material may be approximated with a tensioned string or line.

FIG. 1 shows one embodiment of a prior art system undergoing suture tear-through. An operator may have attempted to close a defect 14 formed between tissue portions 11*a*, 11*b* with a continuous suture line 12. However, tension within the suture line 12 may have caused the suture line 12 to tear through the tissue portion 11*b*. As shown in FIG. 1, tearing of the suture line 12 through the tissue portion 11B not only fails to approximate tissue portions 11*a*, 11*b* to close the defect 14, but also introduces new tears 13 in the tissue portion 11*b*. It should be appreciated that in some prior art system, the suture line 12 may tear through both tissue portions 11*a* and 11*b*.

Figure 2:
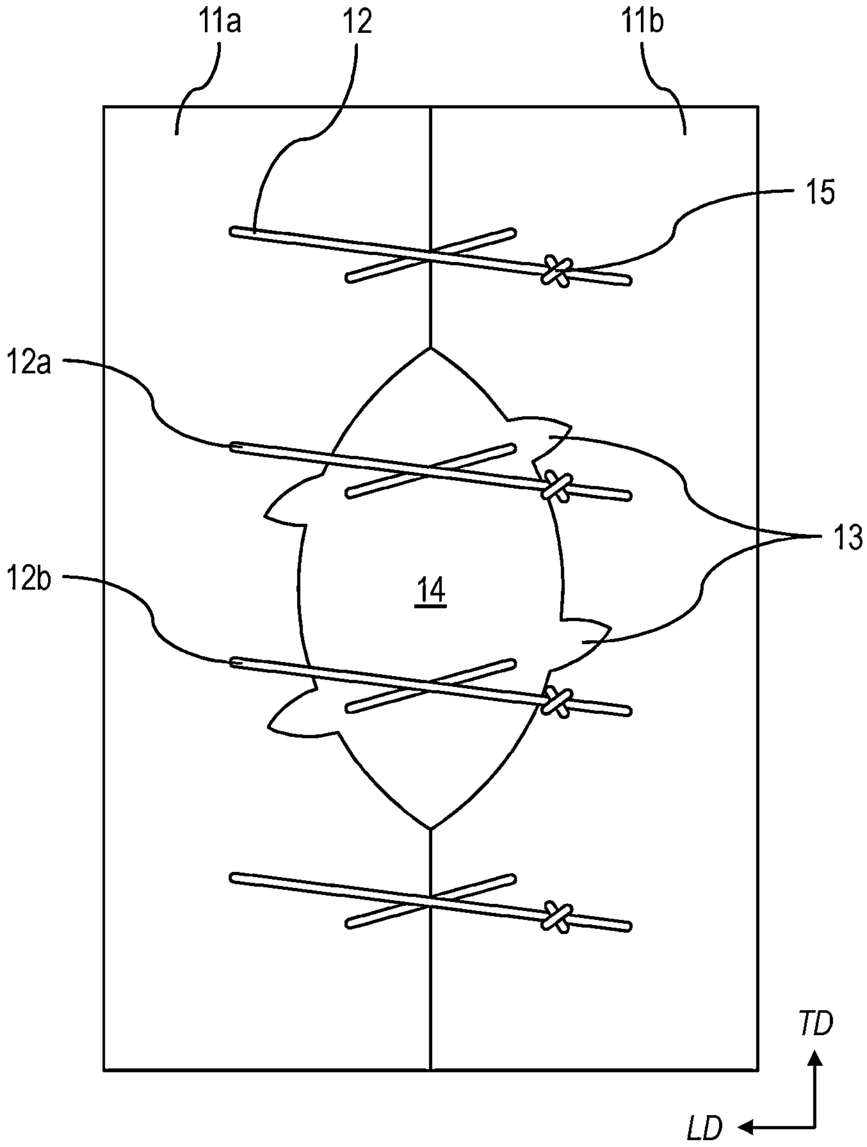
FIG. 2 is a schematic top view of an interrupted suture pattern exhibiting pull-through tears.

FIG. 2 shows one embodiment of a prior art system undergoing suture tear through with an interrupted suture pattern (e.g., pulley stitch). In this embodiment, sutures 12*a*, 12*b* traverse a defect 14 in order to approximate tissue portions 11*a*, 11*b*. However, as shown in FIG. 2, tension within the sutures 12*a*, 12*b* can cause tears 13 and prevent closure of the defect 14.

Figure 3:
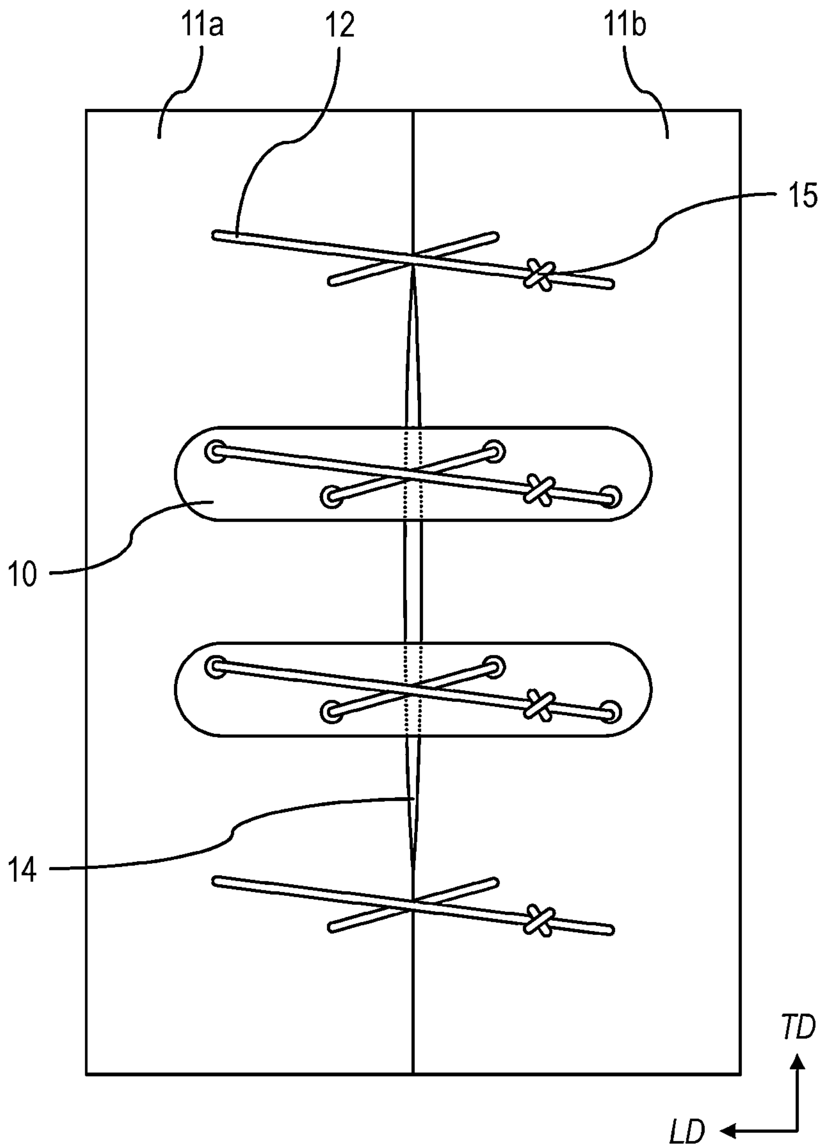
FIG. 3 is a schematic top view of an interrupted suture pattern using one embodiment of a surgical device.

FIG. 3 shows a defect closure using a surgical device according to some embodiments. The surgical device 10 may be used with a pulley stitch pattern across a defect 14 in order to approximate tissue portions 11*a*, 11*b*. The pulley stitch pattern may include a knot 15 after each interrupted suture pass. As shown in FIG. 3, the device 10 may reduce the likelihood of sutures 12 from pulling through the tissue portions 11*a*, 11*b* by distributing the tension within each suture 12 and by acting as a physical barrier against the suture tearing through the tissue due to the associate through holes restraining a location of the sutures at a surface of the tissue the device is disposed on.

It should be appreciated that a surgeon may determine an optimal position for the device 10 along defect 14. In some embodiments, the device 10 may be placed at the widest point of the defect 14, as shown in FIG. 3, where tensile force along the suture line 12 may be greatest. In other embodiments, more than one device 10 may be used to close a defect 14 as shown in the figure where multiple devices and separate sutures are used in combination with one another to close the tissue defect. Thus, it should be appreciated that the current disclosure is not limited by the position, arrangement, or number of device(s) 10 that are positioned along and used to close a defect 14.

Figure 4:
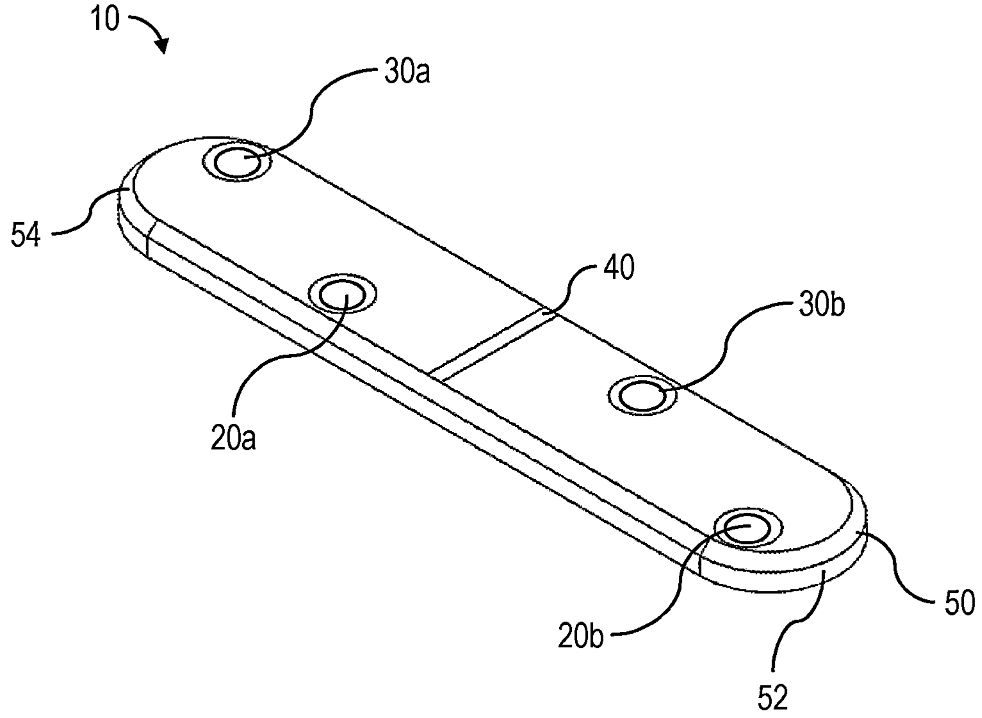
FIG. 4 is a perspective top view of the surgical device of FIG. 3.

FIG. 4 shows a surgical device 10 according to some embodiments. The device 10 may include a plurality of through holes 20*a*, 20*b*, 30*a*, 30*b* to allow a suture to pass through the device. In some embodiments, the device 10 may include a midline marker 40, such as a line or groove extending across at least a portion of a width of the device, at a position located at approximately a position equidistant from opposing ends of the device for alignment purposes. The marker 40 may be visually distinct from the rest of the device 10, such that an operator (e.g., a surgeon), may be able to determine the midline of the device 10 optically. The device 10 may include an elongated body with rounded end portions 52, 54 for ergonomic functionality, though non-linear shapes and/or non-rounded end portions are also contemplated. The device 10 may also include one or more sidewalls 50 extending around a periphery of the device and extending between two opposing surfaces oriented towards and away from the underlying tissue respectively, when the device is disposed on tissue during use.

Figure 5:
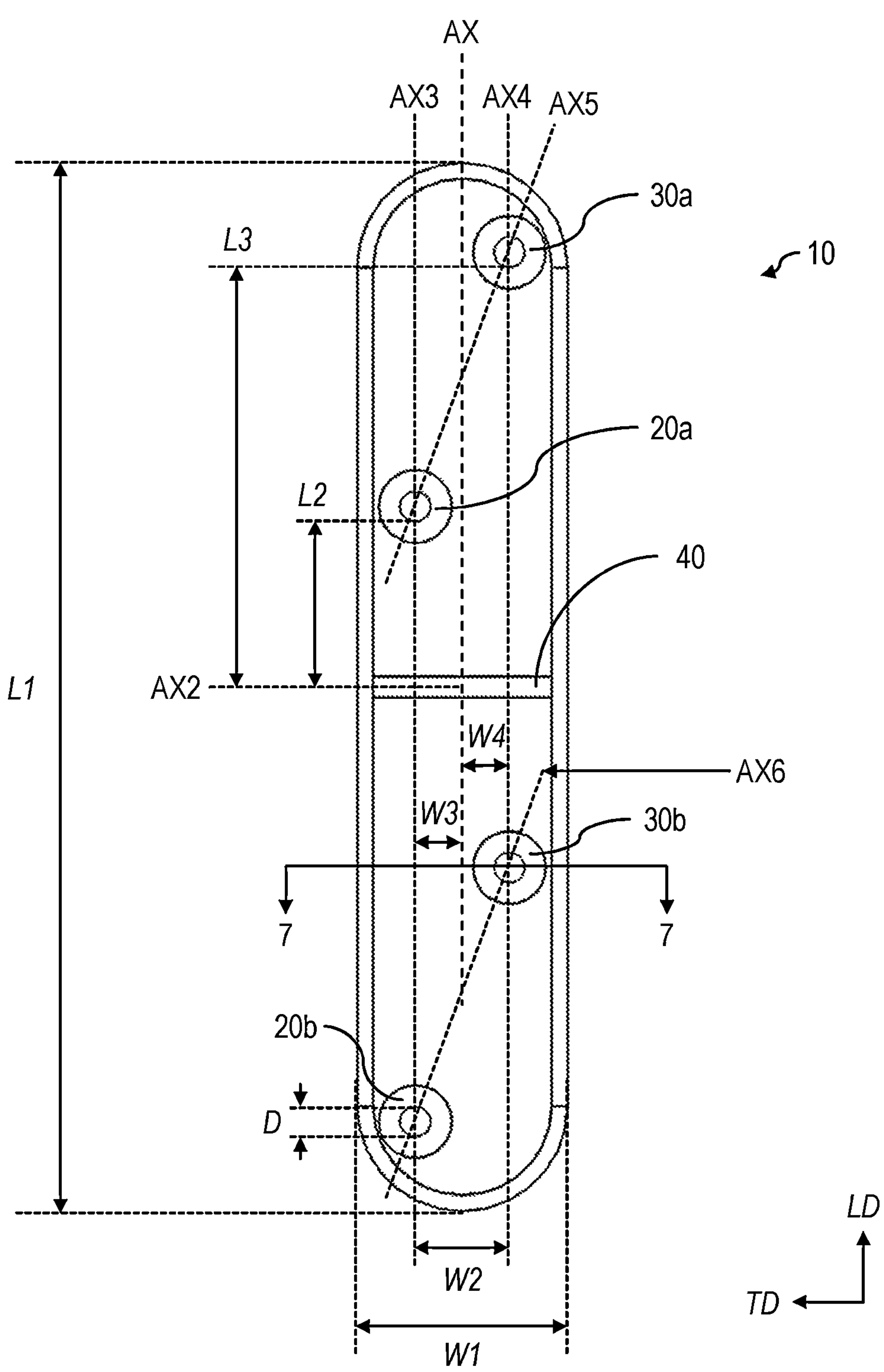
FIG. 5 is a top view of the surgical device of FIG. 3.

As shown in FIG. 5, a device 10 may include an elongated body in some embodiments. In some embodiments, the device 10 may be stadium (e.g., rounded rectangle) shaped, such that end portions 52, 54 may be rounded. In other embodiments, the device 10 may be elliptical (e.g., circular), rectangular (e.g., square), rounded rectangular, rhomboid, trapezoidal, polygonal, curved, any combination thereof, and/or any other suitable shape. It should be appreciated that the device 10 is not limited by the shape of its body, as different applications may use different body shapes.

In some embodiments, the device 10 includes first dimension, such as a length L1, which may be perpendicular to a second dimension, such as width W1. In embodiments where the device 10 has an elongated body, the length L1 of the device 10 may be greater than the width W1. Accordingly, when the device 10 is used with interrupted suture patterns, the device 10 may be oriented such that its length L1 spans a lateral direction LD of the defect 14, and its width W1 spans a transverse direction TD of the defect (shown as defect 14 in FIG. 3). It should be appreciated that while the device 10 is shown to be aligned with the lateral direction LD of the defect 14 in FIG. 3, embodiments where the device 10 is oriented at an angle with respect to the lateral direction LD of the defect 14 are also contemplated. As described in further detail below, the length L1 and width W1 of the device 10 may be any suitable size, as the present disclosure is not so limited.

The device 10 may include a first axis AX (e.g., a longitudinal axis) spanning along the length L1 dimension of the device and a second axis AX2 spanning along the width W1 dimension. It should be appreciated that while the first axis AX and second axis AX2 are shown to be perpendicular in FIG. 5 where they correspond to a longitudinal and transverse axis respectively, other orientations between axis AX and axis AX2 are also contemplated. Axis AX may be located central to the device 10, as shown in FIG. 5, or may be located at any other position with respect to the device. Similarly, in some embodiments, axis AX2 may be located central to the device 10, as shown in FIG. 5, whereas in other embodiments, the axis AX2 may be located at any other position with respect to the device.

According to some embodiments represented by FIG. 5, the device 10 may include at least four through holes 20*a*, 20*b*, 30*a*, 30*b*. Two of the through holes, 20*a* and 30*a*, may be located on one side of the axis AX2, while the other two through holes, 20*b* and 30*b* may be located on the opposing side of the axis AX2. In some embodiments, two of the through holes 20*a* and 20*b* may be located on one side of the axis AX, while the other two through holes 30*a* and 30*b*, may be located on the opposing side of the axis AX. In some embodiments, the device 10 may include at least one through hole in each quadrant formed by the intersection of the axes AX and AX2.

According to some embodiments, through holes 20*a* and 20*b* may be located on the same axis, for example third axis AX3, which may be parallel to the axis AX. In other words, the through holes 20*a* and 20*b* may be aligned along axis AX3. It should be appreciated that embodiments wherein the through holes 20*a* and 20*b* are not aligned along an axis parallel to the axis AX extending along a length of the device are also contemplated. In some embodiments, through holes 30*a* and 30*b* may be aligned along an axis, for example fourth axis AX4, parallel to the axis AX, whereas in other embodiments, through holes 30*a* and 30*b* may not be aligned along an axis parallel to the axis AX. In some embodiments, axes AX3 and AX4, and the associated separate groups of through holes formed along a portion of the length of the device, may be parallel to and offset from one another relative to a width of the device. In some embodiments, the through holes located along the parallel axes AX3 and AX4 may also be staggered relative to one another along a length of the device such that the through holes in each of the separate groups of through holes may be positioned at different positions along a length of the device. Of course, other angled arrangements between axes AX3 and AX4 are also contemplated. As will be described in further detail below, the offset nature of through holes 20*a* and 20*b* from through holes 30*a* and 30*b* in both the longitudinal and transverse directions (i.e., length and width) may reduce the frictional contact between sutures passing through the aforementioned through holes when using certain suturing patterns.

According to some embodiments, axis AX3, and the associated first group of through holes, may be offset from axis AX by a distance W3, as indicated by FIG. 5. The distance W3 may be at least 2 mm, 2.25 mm, 2.5 mm, 2.75 mm, 3 mm, 3.25 mm, 3.5 mm, 3.75 mm, 4 mm, 4.5 mm, 5 mm, or any other suitable size. The distance W3 may also be less than or equal to 5 mm, 4.5 mm, 4 mm, 3.75 mm, 3.5 mm, 3.25 mm, 2.75 mm, 2.5 mm, 2.25 mm, 2 mm, or any other suitable size. Combinations of these ranges are contemplated, including, for example, the distance W3 may be between 4 mm and 5 mm, 3 mm and 5 mm, 3 mm and 6 mm, or any other suitable range of sizes. In some embodiments, distance W3 may be 3 mm. It should be appreciated that distance W3 may be adjusted based on the application, size of the through holes, and/or width W1 of the device 10.

Similar to the above, axis AX4, and the associated second group of through holes, may be offset from axis AX by a distance W4, as indicated by FIG. 5. In some embodiments, distance W3 may be substantially equal to distance W4, such that axis AX3 and axis AX4 are mirrored about axis AX. However, embodiments where distance W4 may be less than or greater than axis AX3 are also contemplated. It should be appreciated that distance W4 may be any suitable size compared to distance W3, as the present disclosure is not so limited.

In some embodiments, an axis, for example fifth axis AX5, extending between first through holes 30*a* and 20*a* of each group of through holes may be angled with respect to the transverse dimension TD, which may be a transverse axis, of the device. Similarly, an axis, for example sixth axis AX6, formed between second through holes 20*b* and 30*b* present in the two separate groups of through holes may be angled with respect to the transverse dimension TD. In some embodiments, both axes AX5 and AX6 may also be angled with respect to the lateral dimension LD, which may be a longitudinal axis of the device that is perpendicular to the transverse axis of the device. In some embodiments, axes AX5 and AX6 may be parallel, as shown in FIG. 5. Of course, non-parallel arrangements of axes AX5 and AX6 are also contemplated. Additionally, embodiments in which more than two through holes are included in the offset groups of through holes are also contemplated. In some embodiments, through holes distributed along axis AX3 (e.g., through holes 20*a* and 20*b*) may be offset from the through holes distributed along axis AX4 (e.g., through holes 30*a* and 30*b*) in the longitudinal direction (e.g., along axis AX). In other embodiments, as described in further detail below, through holes distributed along different longitudinal axes may be aligned with one another.

In some embodiments, a distance measured between the outermost through holes (e.g., through holes 20*a* and 20*b*) on AX3 entails a first portion of L1, while a distance measured between the outermost through holes (e.g., through holes 30*a* and 30*b*) on AX4 entails a second portion of L1. In some embodiments, as depicted by FIG. 5, the first portion and the second portion of L1 may overlap partially. In other words, one through hole (e.g., through hole 20*b*) along axis AX3 may not lie within the second portion of L1 while one through hole (e.g., through hole 30*a*) along axis AX4 may not lie within the first portion of L1. In other embodiments, the first portion and second portion of L1 may be coextensive, such that the two portions substantially overlap.

In some embodiments, through hole 20*a* may be located a distance L2 away from the axis AX2, which may be a midline of the device, as indicated by FIG. 5. The distance L2 may be at least 2.5 mm, 3 mm, 3.5 mm, 3.8 mm, 4 mm, 4.2 mm, 4.5 mm, 4.8 mm, 5 mm, 5.2 mm, 5.5 mm, 6 mm, 7 mm, or any other suitable size. The distance L2 may also be less than or equal to 7 mm, 6 mm, 5.5 mm, 5.2 mm, 5 mm, 4.8 mm, 4.5 mm, 4.2 mm, 4 mm, 3.8 mm, 3.5 mm. 3 mm, 2.5 mm or any other suitable size. Combinations of these ranges are contemplated, including, for example, the distance L2 between 4 mm and 5 mm, 3 mm and 5 mm, 3 mm and 6 mm, or any other suitable range of sizes. It should be appreciated that the distance L2 between through hole 20*a* may be adjusted to suit the application. For example, a very small defect size may require a small bite size compared to a larger defect with a larger defect. Accordingly, the distance L2 may be any suitable size, as the present disclosure is not so limited.

Similarly, through hole 30*a* may be located a distance L3 from the axis AX2 as indicated by FIG. 5. The distance L3 may be at least 5 mm, 6 mm, 7 mm, 8 mm, 9 mm, 10 mm, 11 mm, 12 mm, 15 mm, 20 mm, 25 mm, 30 mm, 40 mm, 50 mm, or any other suitable size. The distance L3 may also be less than or equal to 50 mm, 40 mm, 30 mm, 25 mm, 20 mm, 15 mm, 12 mm, 11 mm, 10 mm, 9 mm, 8 mm, 7 mm, 6 mm, 5 mm, or any other suitable size. Combinations of these ranges are contemplated, including, for example, the distance L3 between 10 mm and 20 mm, 5 mm and 30 mm, 10 mm and 40 mm, or any other suitable range of sizes. In some embodiments, the distance L3 may be 10 mm. As described with reference to distance L2, distance L3 may be any suitable size for any suitable application, as the present disclosure is not limited by the size of distance L3.

In some embodiments, through hole 30*b* may be spaced away from axis AX2 by a distance equal to distance L2. In other words, through holes 30B and 20A may be equidistant from the axis AX2. In other embodiments, through hole 30*b* may be spaced away from axis AX2 by a distance greater than or less than distance L2. Similarly, through hole 20*b* may be spaced away from axis AX2 by a distance equal to distance L3, such that through holes 30A and 20B may be equidistant from axis AX2. Embodiments where through hole 20B and 20B are also contemplated.

In some embodiments, another way of characterizing the positioning of through holes present in separate groups of through holes extending along at least a portion of a length of a device may include a longitudinal offset between corresponding through holes of each group of through holes along a length of the device. For example, in the embodiment of FIG. 5, the through holes in each group are spaced from one another by the same longitudinal offset along a length of the device (e.g., a pitch distance, as described in further detail below). However, the position of each hole relative to a corresponding hole in the other group of through holes may be offset in the longitudinal direction. This may correspond to the difference between dimensions L2 and L3 in the depicted embodiment of FIG. 5. In some embodiments, this difference between corresponding holes in different groups of through holes (e.g., longitudinal offset distance between through holes 20*a* and 30*a*) may be at least 2 mm, 2.5 mm, 3 mm, 4 mm, 5 mm, 6 mm, 7 mm, 8 mm, 10 mm, 12 mm, 14 mm, 15 mm, or any other suitable distance. The longitudinal offset distance between corresponding holes in different groups of through holes may also be less than or equal to 15 mm, 14 mm, 12 mm, 10 mm, 8 mm, 7 mm, 6 mm, 5 mm, 4 mm, 3 mm, 2.5 mm, 2 mm, or any other suitable distance. Combinations of these ranges are also contemplated, including, for example, a longitudinal offset distance between 2 mm and 15 mm, 3 mm and 10 mm, 5 mm and 15 mm, 2 mm and 10 mm, or any other suitable range of distances. It should be appreciated that the longitudinal offset distance between any groups of through holes may be determined by the number of through holes, the length L1 of the device, and the diameter D of the through holes.

As shown in FIG. 5, any group of through holes may be evenly distributed along its respective axes (e.g., group of through holes 20*a* and 20*b* along axis AX3) by a longitudinal pitch distance. In some embodiments, the longitudinal pitch distance of any group of through holes may be 5 mm. In other embodiments, the longitudinal pitch distance of any group of through holes may be at least 4 mm, 5 mm, 6 mm, 7 mm, 8 mm, 9 mm, 10 mm, 11 mm, 12 mm, 13 mm, 14 mm, 15 mm, 16 mm, 20 mm, 22 mm, 25 mm, or any other suitable distance. The longitudinal pitch distance of any group of through holes may also be less than or equal to 25 mm, 22 mm, 20 mm, 16 mm, 15 mm, 14 mm, 13 mm, 12 mm, 11 mm, 10 mm, 9 mm, 8 mm, 7 mm, 6 mm, 5 mm, 4 mm, or any other suitable distance. Combinations of these ranges are also contemplated, including, for example, the longitudinal pitch distance of any group of through holes between 5 mm and 20 mm, 4 mm and 10 mm, 5 mm and 15 mm, or any other suitable range of distances. It should be appreciated that the longitudinal pitch distance of any group of through holes may be determined by the number of through holes, the length L1 of the device, and the diameter D of the through holes. Of course, embodiments where any of the groups of through holes are not evenly spaced along any respective axis are also contemplated, as the present disclosure is not so limited. In some embodiments, a pitch distance measured for a first group of through holes may be equivalent to a pitch distance measured for a second group of through holes. Of course, embodiments in which groups of through holes have different pitch distances are also contemplated.

As described in detail further below, through holes 20*a*, 20*b*, 30*a*, and 30*b* may have any suitable diameter D. It should be appreciated that while circular through holes are shown in FIG. 5, any other suitable shape may be used to allow the device 10 to distribute tension from sutures passing through the through holes. In some embodiments, through holes 20*a*, 20*b*, 30*a*, and 30*b* may all have the same diameter D, as shown in FIG. 5, whereas in other embodiments, through holes 20*a*, 20*b*, 30*a*, and 30*b* may be differently sized. The current disclosure is not limited by the shape, size, number, or location of the through holes.

According to some embodiments, the midline 40 of the device 10 relative to the through holes formed in the device may be located centrally along an overall length L1 of the device. In other embodiments, the midline 40 may be located at any other position along length L1. The midline 40 may have any suitable optical properties in order to be optically distinguishable. For example, the midline 40 may have a different color, opacity, material, or surface structure when compared to the rest of the device 10. In embodiments where the device is positioned along a transverse direction of the defect (e.g., FIG. 10), the device may not include a midline 40. It should be appreciated that the current disclosure is not limited by the presence, position, or optical properties of the midline 40.

Figure 6:
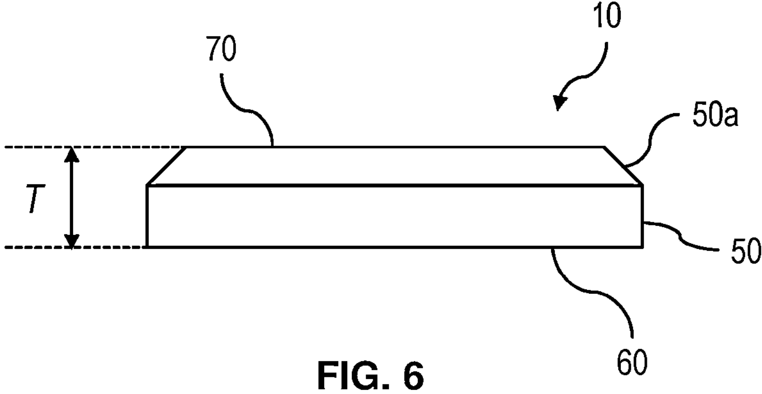
FIG. 6 is a front view of the surgical device of FIG. 3.

FIG. 6 shows a side view of the device 10 according to some embodiments. The device may have a thickness T, measured from a bottom surface 60 of the device oriented towards an underlying supporting surface (e.g., tissue) to the top surface 70 oriented away from the underlying supporting surface. Although a uniform thickness T is shown in FIG. 6, embodiments with variable thickness T across the device 10 are also contemplated. For example, top surface 70 may not be parallel to bottom surface 60. In some embodiments, the top surface 70 and/or bottom surface 60 may include surface features to improve adhesion with the surrounding environment. For example, bottom surface 60, which may be in contact with tissue, may include surface features such as grooves, ridges, or other surface textures configured to better grip tissue. In some embodiments, bottom surface 60 may be smooth to allow the device 10 to laterally move around during a suturing process.

As will be described in greater detail below, the thickness T may be any suitable size with respect to the application of the device 10. Device 10 may also include a beveled, chamfered, or rounded edge 50*a* extending between its sidewall 50 and top surface 70. It should be appreciated that the sidewall 50 may be formed with any desired type of edge (either between the bottom surface 60 and the sidewall 50 and/or between the top surface 70 and the sidewall 50), as the present disclosure is not so limited.

Figure 7:
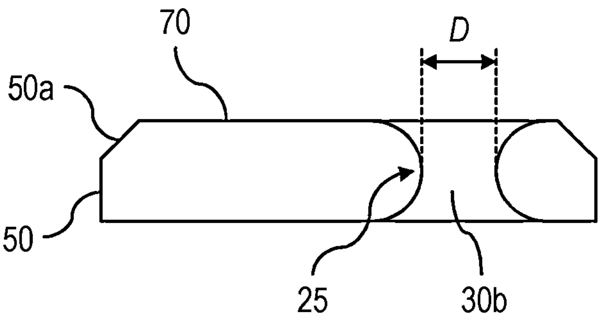
FIG. 7 is a cross-section of the surgical device of FIG. 5 taken along line 7-7.

FIG. 7 shows a cross-sectional view of device 10 from FIG. 5, taken along line 7-7 and through hole 30*a*. In some embodiments, through hole 30*b* (and any other through hole) extends from the bottom surface 60 (which may be in contact with the defect site) to the top surface 70. The through hole 30*b* (or any other through hole) may a rounded or curved internal surface with an internal radius 25 to accommodate a suture passing through the through hole without creating stress concentration and/or snagging points along a length of the associated suture line. For example, a sharp edge between the through hole 30*b* sidewall and the top surface 70 may increase tensile and/or shear stresses within a suture line passing through 30*b* and may cause the suture line to break. In some embodiments, the internal radius 25 may be substantially equal to half of the thickness H of device 10, as depicted in FIG. 5, although other embodiments of the internal radius 25 are also contemplated.

Figures 8A, 8B:
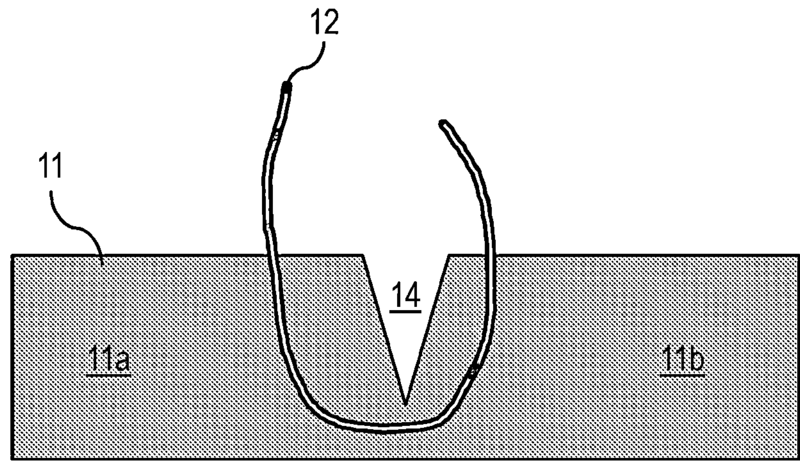
FIGS. 8A-8F are schematic views depicting a method of wound closure using the surgical device of FIG. 3.

FIGS. 8A-8F depict a method of use for device 10 according to some embodiments. As shown in FIG. 8A, an operator (e.g., surgeon), may seek to close a defect 14 formed between tissue portions 11*a*, 11*b*. Accordingly, the operator may thread a suture 12 into tissue portion 11*a* and out of tissue portion 11*b* using a needle (not shown) or any other suitable tissue puncturing means. In some embodiments, a bite size on tissue portion 11*a*, measured from the defect edge to a puncture point of a needle and/or suture into tissue 11, may be substantially equal to a bite size on tissue portion 11*b*. Next, a device 10 may be threaded onto the suture 12, or vice versa, as shown in FIG. 8B. In some embodiments, the midline 40 (as shown in FIG. 5) may facilitate the operator's alignment of the device 10 with the defect 14 and the suture 12. In other embodiments, the device 10 may include any other optical properties to enable alignment. For example, the device 10 may be transparent or translucent to allow the operator to visualize the defect through the device 10. In some embodiments, the suture 12 may pass through holes 30*a* and 30*b* in the step depicted in FIG. 8B. In other embodiments, the suture 12 may pass through holes 20*a* and 20*b* in the steps depicted in FIG. 8B. It should be appreciated that the suture 12 may pass through any pattern of through holes according to the suitable suture pattern used. For example, the suture 12 may pass through holes 20*a* and 30*b* in the step depicted in FIG. 8B. As described above, the device 10 or associated method of operation is not limited by the suture pattern.

Figure 8C:
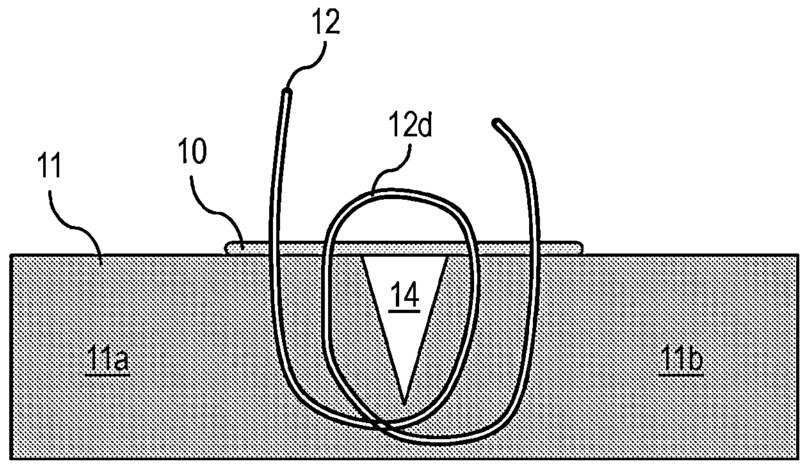
Figure 8D:
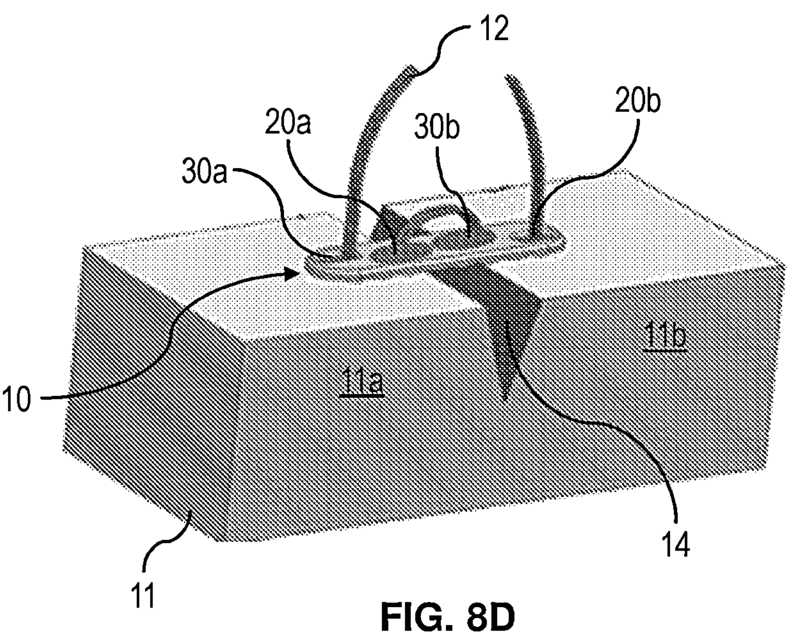
Figure 8E:
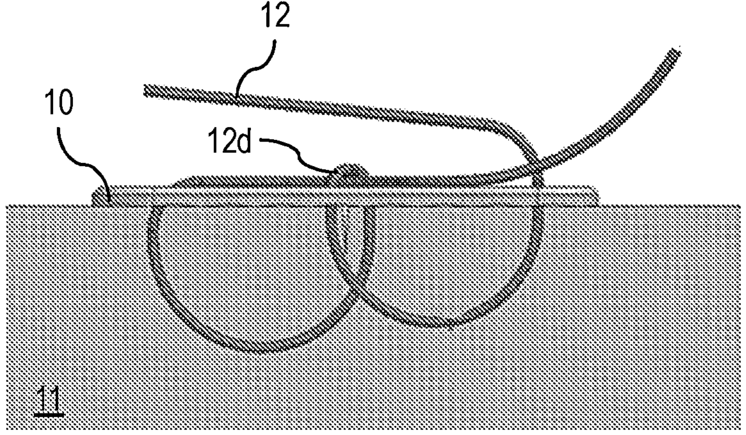
Figure 8F:
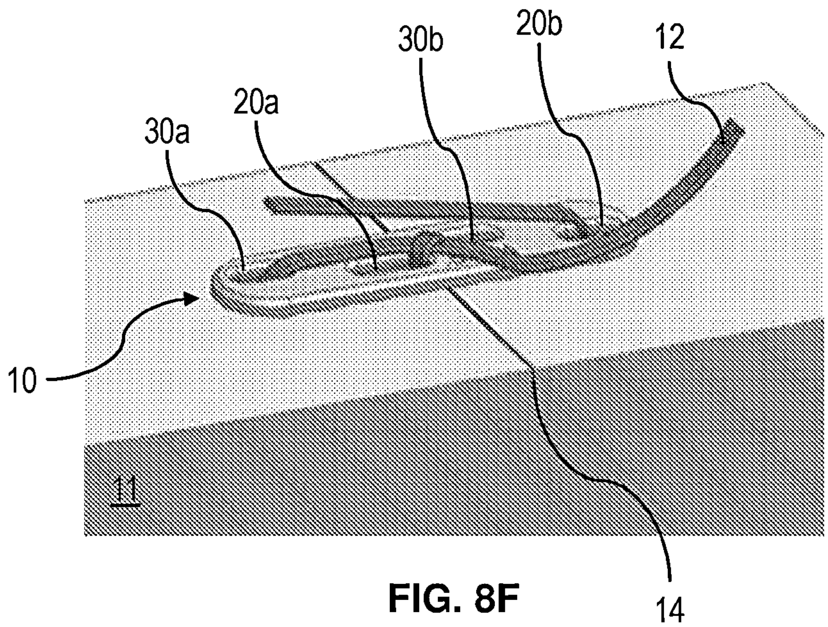

As shown in FIG. 8C, the operator may continue passing the suture 12 through the remaining through holes. As shown in FIG. 8D, the operator may pass the suture 12 into hole 30*a*, out of hole 30*b*, into hole 20*a*, and out of hole 20*b*, following a far-near-near-far suture pattern. The suture 12 may not be experiencing sufficient tension to close the defect 14 in the step shown in FIG. 8D. Accordingly, a suture loop 12*d* may be formed between two of the through holes, as indicated on FIG. 8C. Although suture loop 12*d* is shown between through holes 20*a* and 30*b*, it should be appreciated that the suture loop 12*d* may be located between any other pair of through holes. In some embodiments, the suture 12 may include more than one suture loop 12*d*. As shown in FIG. 8E, the operator may be able to thread one end of the suture 12 through the suture loop 12*d* in order to approximate the tissue portions and close the defect 14. In some embodiments, the suture 12 may not need to pass through a suture loop 12*d* in order to approximate the tissue portions 11*a*, 11*b*. The free ends of the suture 12 may be tensioned and knotted to further tension the suture 12 and fix it in place (as shown with knot 15 in FIG. 3), although other methods of tensioning and fixing the suture 12 are also contemplated.

Figure 9:
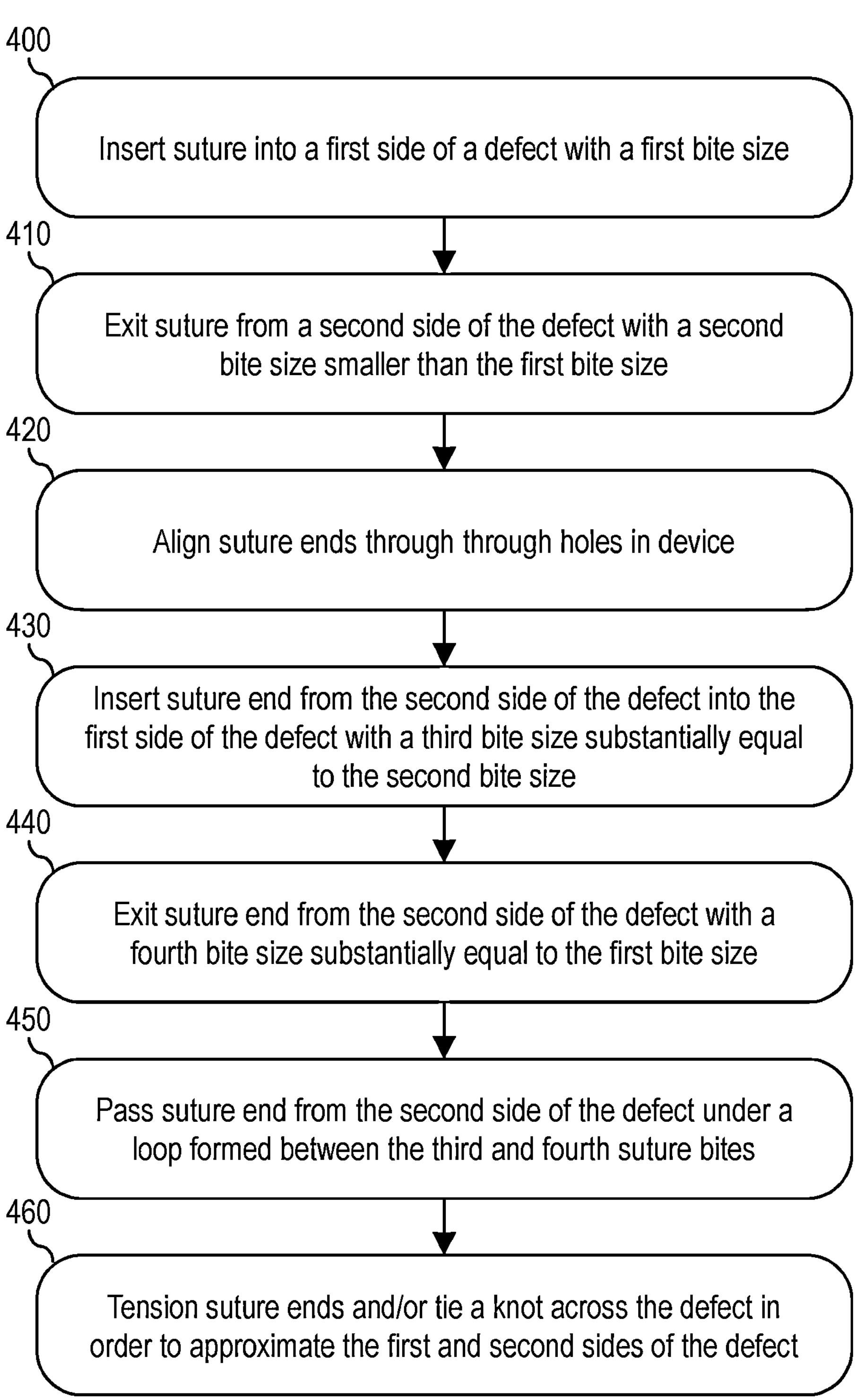
FIG. 9 shows, according to some embodiments, a flow chart for a method of wound closure using a surgical device.

FIG. 9 shows, according to some embodiments, a flow chart for a defect closure method using a far-near-near-far suture pattern using a surgical device. In block 400, a suture may be inserted into tissue from a first side (e.g., tissue portion 11*a*, as shown in FIG. 8D) of a defect (e.g., defect 14, as shown in FIG. 8D). The suture may then exit the tissue from a second side (e.g., tissue portion 11*b*, as shown in FIG. 8D), as depicted in block 410. In these embodiments, a first bite size on the first side may be greater than a second bite size on the second side. In block 420, a device (e.g., device 10, as shown in FIG. 8D) may be aligned and passed through a pair of suture ends extending from the tissue. In some embodiments of the method shown in FIG. 9, one suture end may pass through one of through holes 20*a* or 30*b* as the other suture end passes through one of through holes 20*b* or 30*a* (shown in FIG. 8F). In block 430, the suture end from the second side of the defect may be inserted into the first side of the defect with a third bite size substantially equal to the second bite size. In block 440, the suture end from block 430 may pass across the tissue and/or defect and exit from the second side of the defect with a fourth bite size substantially equal to the first bite size. In block 450, the suture end from the second side of the defect may pass under a loop (e.g., loop 12*d* in FIG. 8C) formed between the third and fourth suture bites (described in blocks 530 and 540, respectively). Passing the suture end under the loop (e.g., in between the top surface of the device and the loop) may allow the suture to temporarily hold tension when approximating the tissue, prior to formal closure (e.g., suture knotting) of the defect. As described earlier and as depicted in block 460, the suture ends may be tensioned across the defect, with suture ends tensioned in opposing directions and/or tied in a knot to approximate the first and second sides of the defect, which may allow for defect closure. In some embodiments, the arrangement of through holes on the device may allow the suture to pass through each through hole without interference between suture lines when taking subsequent suture bites. In other words, a through hole arrangement on the device may prevent suture lines from intersecting with their own paths (e.g., in between bites) until the final passing of a suture end under a suture loop. The lack of self-intersections and/or self-interference of the suture lines may allow the suture line to directly contact the device on the top surface and resist in-line movement of the suture in between the fourth bite and wound closure, which may cause slack in the suture line and improper suture closure.

Figure 10:
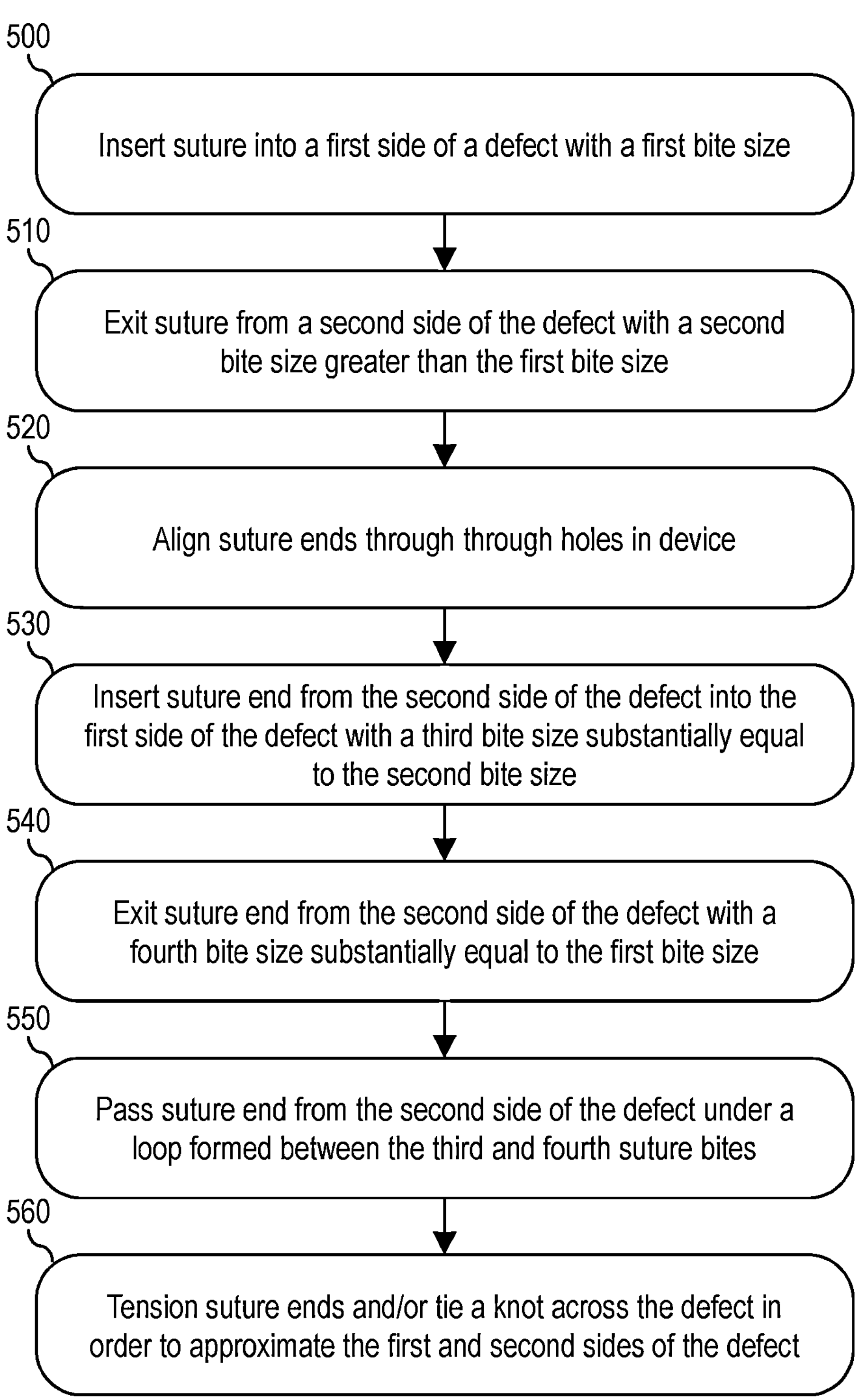
FIG. 10 shows, according to some embodiments, a flow chart for another method of wound closure using a surgical device.

FIG. 10 shows, according to some embodiments, a flow chart for a defect closure method using a near-far-far-near suture pattern using a surgical device. In block 500, a suture may be inserted into tissue from a first side of a defect. The suture may then exit the tissue from a second side, as depicted in block 510. In these embodiments, a first bite size on the first side may be smaller than a second bite size on the second side. In block 520, a device may be aligned and passed through a pair of suture ends extending from the tissue. In some embodiments of the method shown in FIG. 10, one suture end may pass through one of through holes 20A or 30B as the other suture end passes through one of through holes 20*b* or 30*a* (shown in FIG. 8F). In block 530, the suture end from the second side of the defect may be inserted into the first side of the defect with a third bite size substantially equal to the second bite size. In block 540, the suture end from block 530 may pass across the tissue and/or defect and exit from the second side of the defect with a fourth bite size substantially equal to the first bite size. In block 550, the suture end from the second side of the defect may pass under a loop formed between the third and fourth suture bites (described in blocks 530 and 540, respectively) in order to temporarily tension the suture prior to formal closure of the defect. As described earlier and as depicted in block 560, the suture ends may be tensioned and/or tied in a knot across the defect to approximate and fix the first and second sides of the defect, which may enable defect closure. In some embodiments, tension may be applied to both suture ends in opposing directions to facilitate defect closure.

Figure 11:
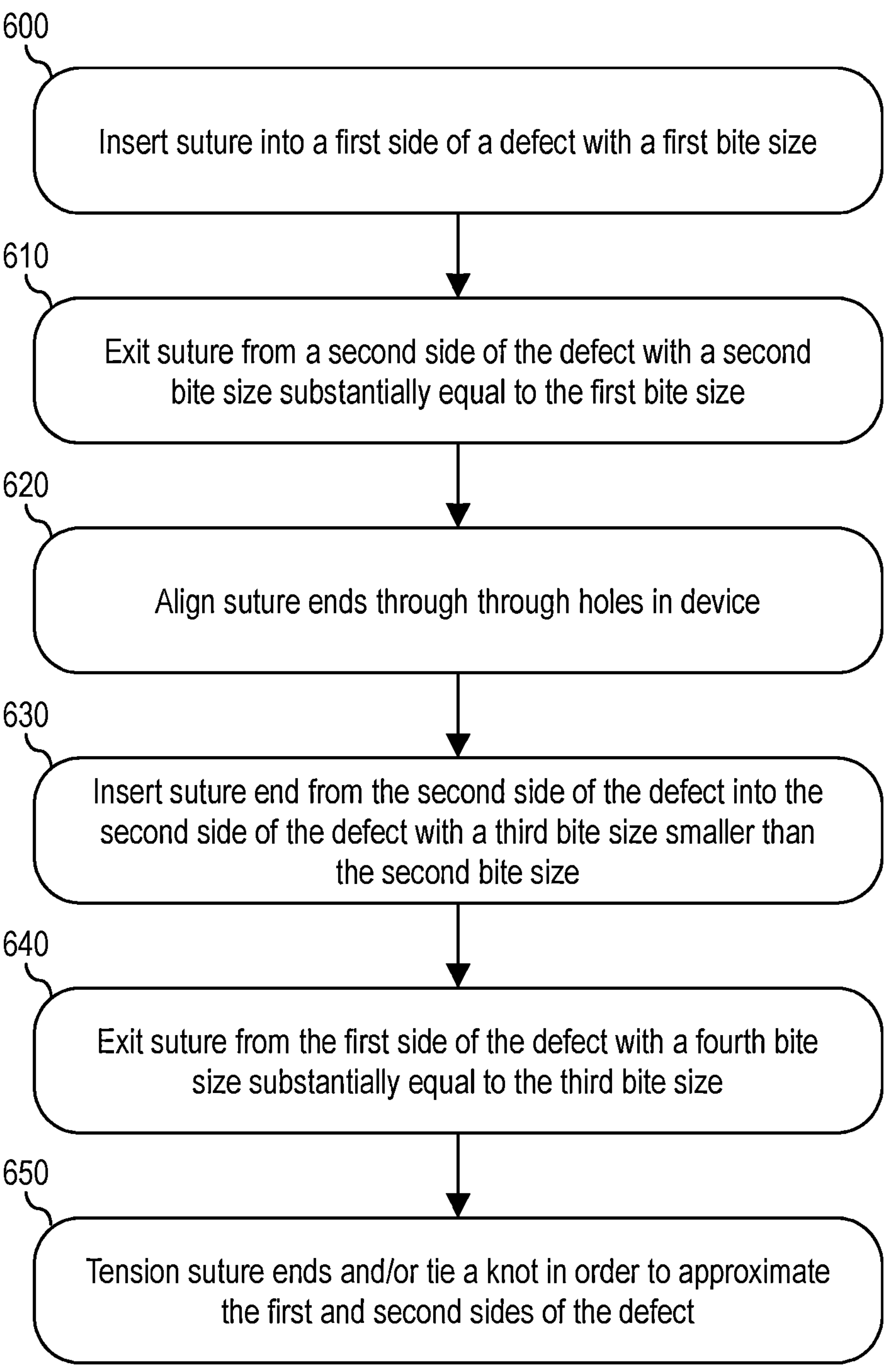
FIG. 11 shows, according to some embodiments, a flow chart for yet another method of wound closure using a surgical device.

FIG. 11 shows, according to some embodiments, a flow chart for a defect closure method using a vertical mattress suture pattern using a surgical device. In block 600, a suture may be inserted into tissue from a first side of a defect. The suture may then exit the tissue from a second side, as depicted in block 610. In these embodiments, a first bite size on the first side may be substantially equal to a second bite size on the second side. In block 620, a device may be aligned and passed through a pair of suture ends extending from the tissue. In some embodiments of the method shown in FIG. 11, the suture ends may pass through through holes 20*b* and 30*a* (shown in FIG. 8F). In block 630, the suture end from the second side of the defect may be inserted into the second side of the defect with a third bite size smaller than the second bite size. In block 640, the suture end from block 630 may pass across the tissue and/or defect and exit from the first side of the defect with a fourth bite size substantially equal to the third bite size. As described earlier and as depicted in block 650, the suture ends may be tensioned and/or tied in a knot to approximate the first and second sides of the defect, which may enable defect closure.

Figure 12:
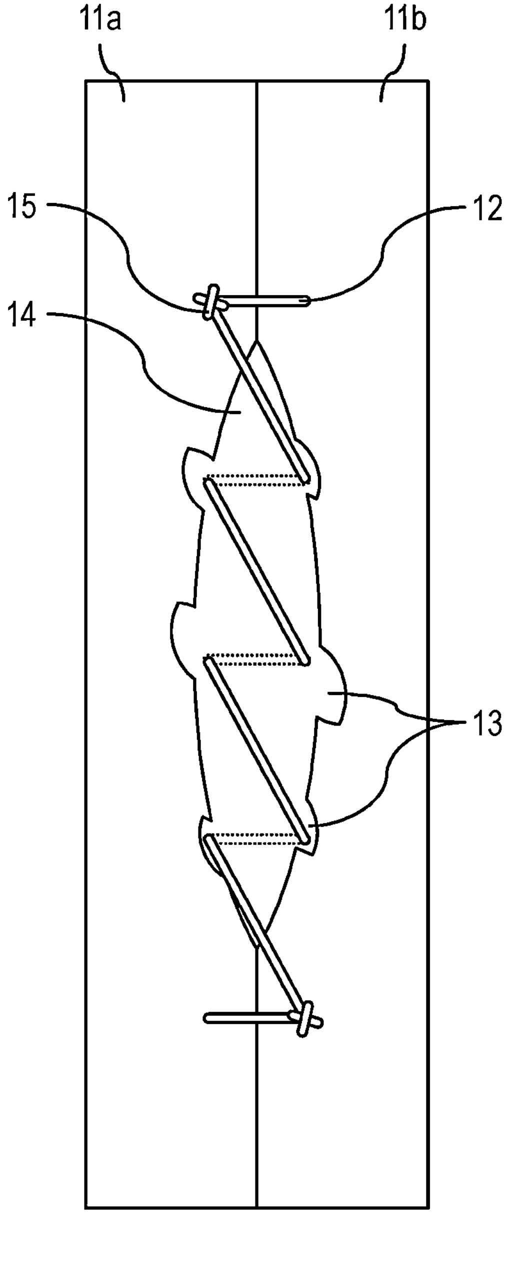
FIG. 12 is a schematic top view of a continuous suture pattern exhibiting pull-through tears.
Figure 12:
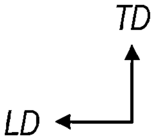

Although some embodiments of the surgical device 10 described herein may be used with interrupted suture patterns, other embodiments of the device may be used with continuous suture patterns. FIG. 12 shows one embodiment of a prior art system undergoing suture tear-through when an operator may have attempted to close a defect 14 formed between tissue portions 11*a*, 11*b* with a continuous suture line 12. As shown in FIG. 12, excess tension within the suture line 12 may cause tears 13 throughout the tissue, which may not only prevent defect closure, but may cause additional damage to the nearby tissue.

Figure 13:
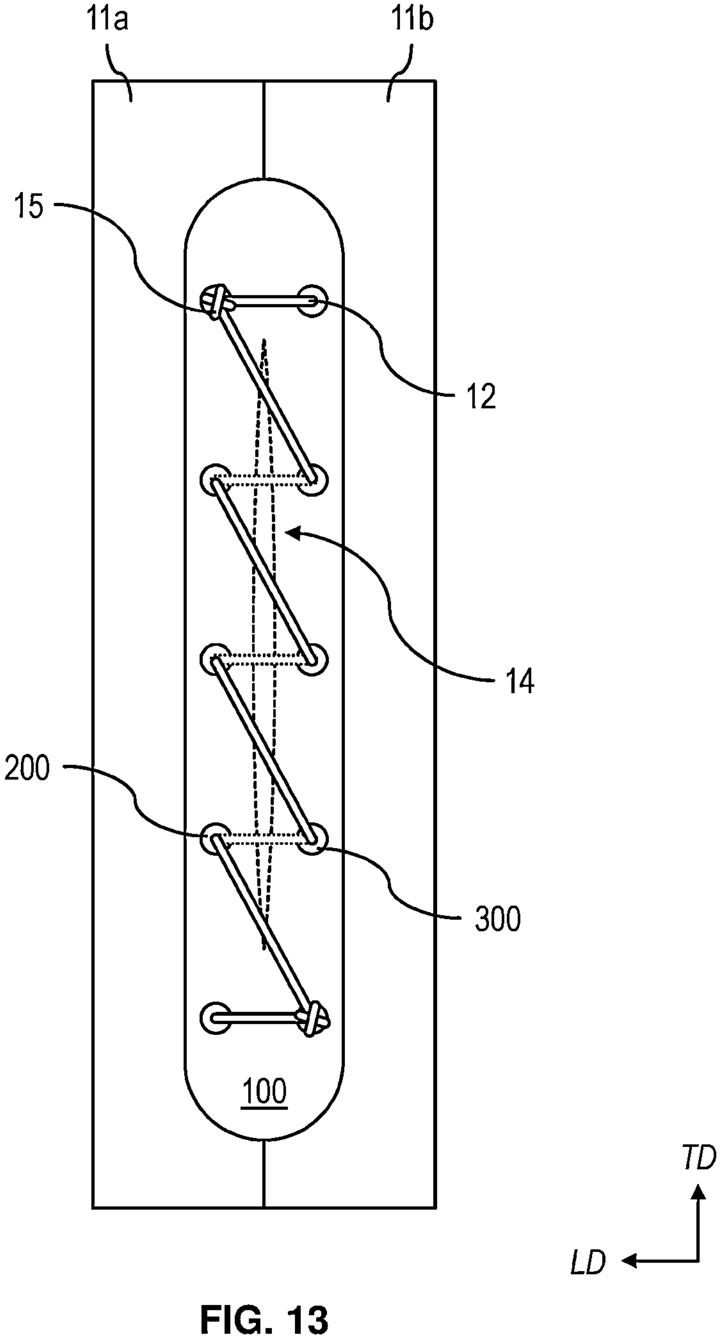
FIG. 13 is a schematic top view of a continuous suture pattern using one embodiment of a surgical device.

Accordingly, in some embodiments, a device 100 may be used with a continuous suture line, as shown in FIG. 13. The suture line 12 may repeatedly pass between tissue portions 11A, 11B through a defect 14 and device 100, and may be tied into knots 15 to tension or otherwise tighten the suture line 12. In these embodiments, the device 100 may be used by alternatingly passing sutures between through holes located in two separate groups of through holes extending along at least a portion of a length of the device and that are offset from one another in the transverse dimension. Thus, as shown in the figure, suture line 12 may pass from through holes 200 located on one side of the defect 14 to through holes 300 located on another side of the defect 14 once it is in the closed, or approximated, configuration with the two portions of the defect positioned adjacent to one another. In the depicted embodiment, the through holes positioned on opposing sides of the defect are aligned with one another such that the groups of through holes are not offset from one another in the longitudinal direction along a length of the device, though embodiments in which longitudinal offsets are used are also contemplated. Although a simple continuous suture pattern (also known as over-and-over suture pattern) is depicted in FIG. 13, any other continuous suture pattern, including, but not limited to ford interlocking, continuous horizontal mattress, continuous vertical mattress, continuous Lembert, Cushing, Connell, Purse-string, Halsted, lock-stitch, or any other suitable suture pattern may be employed with any of the devices described herein.

It should be appreciated that while a single device 100 is shown along defect 14 in FIG. 13, other suitable arrangements of one or more devices are also contemplated. For example, a device which may be smaller than the tissue defect 14 in a transverse direction TD may be employed, covering the widest portion of the tissue defect 14. In another example, a device which may be greater than the tissue defect 14 in the transverse direction TD may be employed. In these embodiments, the elongated body of the device may facilitate defect closure and reduce risk of contamination by covering the defect. Of course, any other arrangement and/or orientation of the device with respect to the tissue defect 14 may also be employed, as the present disclosure is not so limited.

Figure 14:
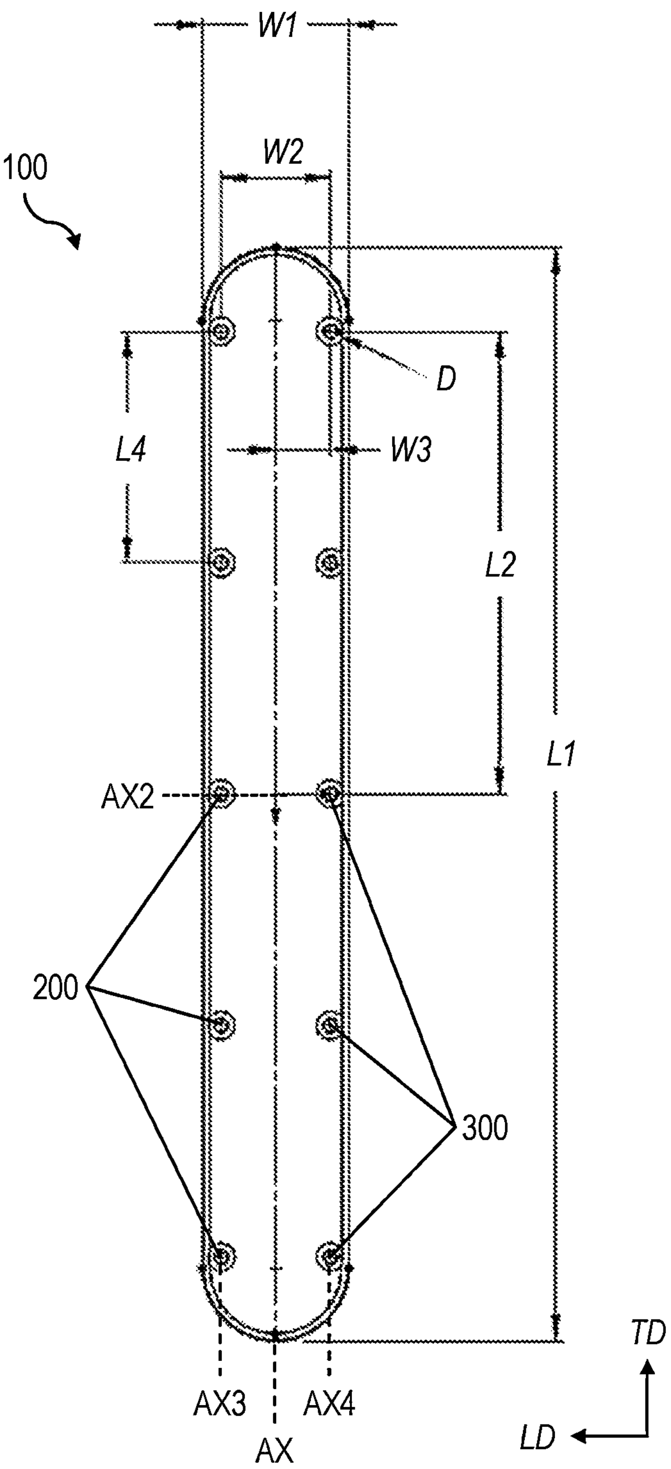
FIG. 14 is a top view of the surgical device from FIG. 13.
Figure 15:
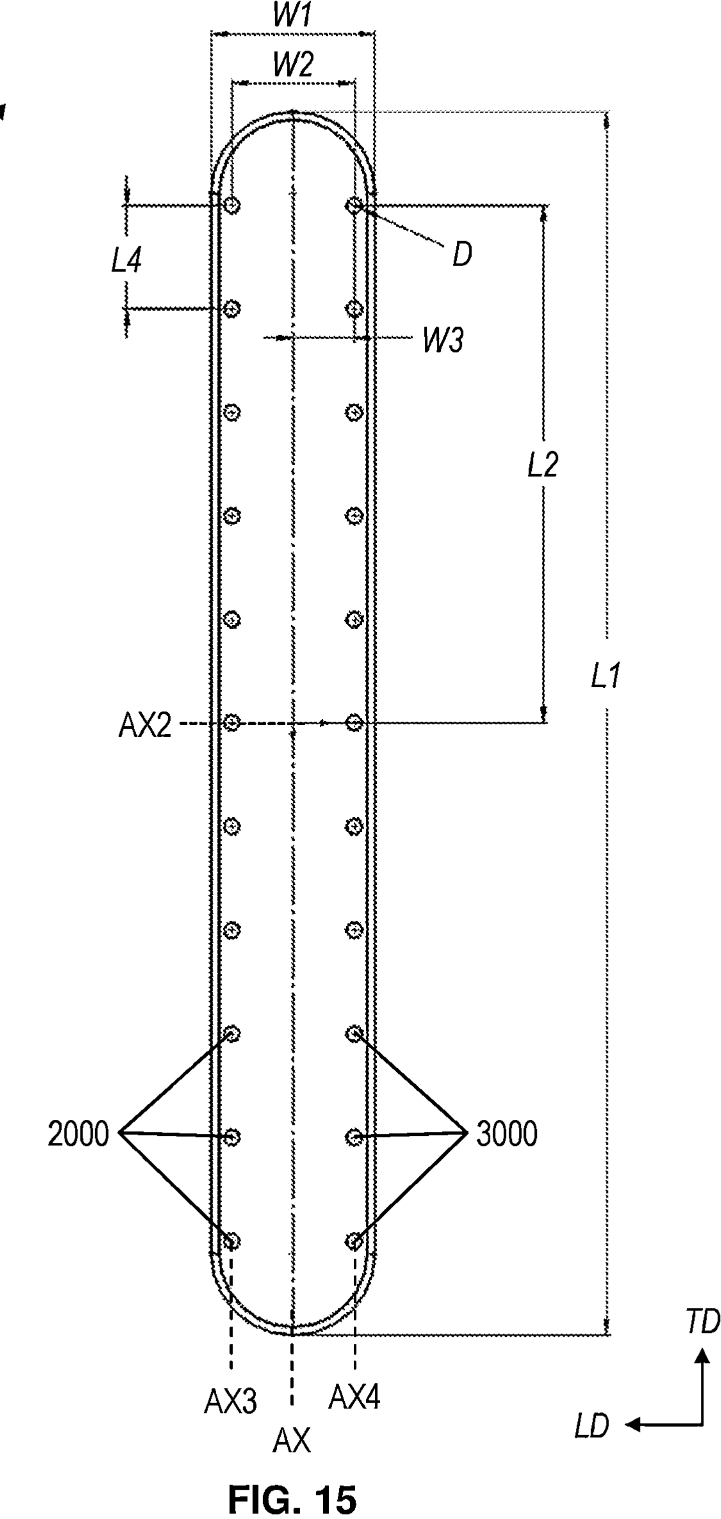
FIG. 15 is a top view of another embodiment of a surgical device.

As shown in FIGS. 14 and 15, a surgical device 100, 1000 may include a length L1 extending along an axis AX. It should be appreciated that in these embodiments of the device 100, axis AX may extend parallel to the transverse direction TD of the defect and may be parallel to a longitudinal axis of the device, as opposed to the lateral direction LD, or transverse axis of the device. This is opposite relative to the configurations described above for FIGS. 3 and 5. The device 100, 1000 may also include a width W1 extending along an axis AX2, e.g., a transverse axis of the device. In some embodiments, axis AX, which may be a longitudinal axis of the device, may be perpendicular to axis AX2, as shown in FIGS. 14 and 15, although other arrangements of axes AX and AX2 are also contemplated.

Device 100, 1000 may include a plurality of through holes 200, 2000 aligned along an axis AX3 extending along a portion of the length of the device, which may be parallel to axis AX, and a separate plurality of through holes 300, 3000 extending along a portion of the length of the device and aligned along an axis AX4, parallel to axis AX. In some embodiments, axes AX3 and AX4 may be mirrored across axis AX, such that a distance W2 measured between axes AX3 and AX4 may be equal to twice the distance W3 between axis AX4 and axis AX. In some embodiments, the distance W2 may be at least 6 mm. Of course, embodiments where axes AX3 and AX4 are not mirrored along axis AX are also contemplated. Although the plurality of through holes 200, 2000 and through holes 300, 3000 are shown to be mirrored across axis AX in FIGS. 14 and 15, other configurations of the through holes are also contemplated. As described in greater detail below, each of the plurality of through holes may have the same diameter D, or may have any combination of diameters, as the present disclosure is not so limited.

In the depicted embodiments in FIGS. 14 and 15, the devices include at least five through holes in each separate group of through holes extending along a portion of a length of the device. However, any appropriate number of through holes may be included in any of the devices disclosed herein. For example, a surgical device according to the current disclosure may include at least two, three, four, five, six, seven, eight, nine, ten, eleven, twelve, thirteen, fourteen, fifteen, sixteen, seventeen, eighteen, nineteen, twenty, or any other suitable number of through holes in a group of through holes extending along a length of the device. A surgical device may also include less than or equal to twenty, nineteen, eighteen, seventeen, sixteen, fifteen, fourteen, thirteen, twelve, eleven, ten, nine, eight, seven, six, five, four, three, two, or any other suitable number of through holes in the separate groups of through holes. It should be appreciated that the devices described herein are not limited by the number of through holes.

As discussed above, through holes distributed along any axis may be aligned or offset with through holes distributed along any other axis in the longitudinal direction (e.g., along axis AX). For example, as seen in FIGS. 14 and 15, through holes 200, 2000 distributed along axis AX3 are aligned with through holes 300, 3000 along axis AX4. Of course, embodiments in which through holes on longitudinal axes are offset to one another (as shown in FIG. 5), are also contemplated.

In some embodiments of device 100, 1000, an outermost through hole may be located a distance L2 away from a midline of the device, e.g., axis AX2, as shown in FIGS. 14 and 15. In some embodiments, distance L2 is 3 cm. The distance L2 may be at least 0.5 cm. 1 cm, 1.25 cm, 1.5 cm, 1.75 cm, 2 cm, 2.25 cm, 2.5 cm, 2.75 cm, 3 cm, 3.5 cm, 4 cm, or any other suitable size. The distance L2 may also be less than or equal to 4 cm. 3.5 cm, 3 cm, 2.75 cm, 2.5 cm, 2.25 cm, 2 cm, 1.75 cm, 1.5 cm, 1.25 cm, 1 cm, 0.5 cm, or any other suitable size. Combinations of these ranges are also contemplated, including, for example, a distance L2 that is between 1 cm and 3 cm, 0.5 cm and 4 cm, or any other suitable range of sizes.

As shown in FIGS. 14 and 15, the plurality of through holes 200, 2000, 300, 3000 within each group of through holes may be evenly spaced from one another by a distance L4 (e.g., a pitch distance). In some embodiments, the distance L4 may be 12.7 mm. In other embodiments, the distance L4 may be 5 mm. In some embodiments, the distance L4 may be at least 4 mm, 5 mm, 6 mm, 7 mm, 8 mm, 9 mm, 10 mm, 11 mm, 12 mm, 13 mm, 14 mm, 15 mm, 16 mm, or any other suitable size. The distance L4 may also be less than or equal to 16 mm, 15 mm, 14 mm, 13 mm, 12 mm, 11 mm, 10 mm, 9 mm, 8 mm, 7 mm, 6 mm, 5 mm, 4 mm, or any other suitable size. Combinations of these ranges are also contemplated, including, for example, a distance L4 that is between 4 mm and 15 mm, 5 mm and 12 mm, or any other suitable range of sizes. It should be appreciated that the distance L4 may be determined by the number of through holes, the length L1 of the device, and the diameter D of the through holes. Of course, embodiments where any of the plurality of through holes 200, 2000, 300, 3000 are not evenly spaced along any respective axis are also contemplated, as the present disclosure is not so limited.

It should be appreciated that the current disclosure is not limited by the size of the suture line. In some embodiments, the suture line may be any suitable standard defined by the United States Pharmacopeia (U.S.P.), including, but not limited to, 11-0, 10-0, 9-0, 8-0, 7-0, 6-0, 5-0, 4-0, 3-0, 2-0, 0, 1, 2, 3, 4, 5, 6, 7. Accordingly, diameter D of any through holes of a device may be sized to fit a specific size of the suture line. In some embodiments, a diameter D of the through holes may be at least 1, 1.25, 1.5, 1.75, or any other suitable multiple of a diameter of the suture line. Correspondingly, the diameter D of any through holes may be less than or equal to 2, 1.75, 1.5, 1.25, or any other suitable multiple of the diameter of the suture line. Combinations of the foregoing ranges are also contemplated, including, for example, the diameter of the through holes between 1 and 2 times a diameter of an associated suture line. The diameter D of the through holes may be 1.5 times the diameter of the suture line. In some embodiments, a through hole diameter greater than 3 times the suture diameter may prevent accurate suture placement and may not properly distribute the suture tension.

In some embodiments, a diameter D of any through hole of a device may be at least 0.02 mm. 0.03 mm, 0.04 mm, 0.05 mm, 0.06 mm, 0.07 mm, 0.08 mm, 0.1 mm, 0.15 mm. 0.12 mm, 0.14 mm, 0.16 mm, 0.2 mm, 0.3 mm, 0.35 mm, 0.4 mm, 0.5 mm, 0.6 mm, 0.7 mm. 0.8 mm, 1 mm, 1.2 mm, 1.4 mm, 1.6 mm, 2 mm, or any other suitable diameter. Correspondingly, the diameter D of any through holes may be less than or equal to 2 mm, 1.6 mm, 1.4 mm, 1.2 mm, 1 mm, 0.8 mm, 0.7 mm, 0.6 mm, 0.5 mm, 0.4 mm, 0.35 mm, 0.3 mm, 0.2 mm, 0.16 mm. 0.14 mm, 0.12 mm, 0.15 mm, 0.1 mm, 0.08 mm, 0.07 mm, 0.06 mm, 0.05 mm. 0.04 mm, 0.03 mm, 0.02 mm, or any other suitable diameter. Combinations of the foregoing ranges are also contemplated, including, for example, a diameter of any through hole being between 0.02 mm and 2 mm, 0.05 mm and 1 mm, 0.05 mm and 1.2 mm, 0.06 mm and 2 mm, 0.02 mm and 0.7 mm, or any other suitable range of sizes.

In some embodiments, as shown in FIGS. 5, 14, and 15, a plurality of through holes on any given device may have the same diameter D. In this way, manufacturing processes may be simplified. In other embodiments, different through holes on the same device may have different diameters. Variation in through hole diameter may allow adjustment of the suture line in some through holes (e.g., distal through holes 30*a* and 20*b* in FIG. 5) which may be larger than other through holes (e.g., proximal through holes 20*a* and 30*b* in FIG. 5) during a defect closure procedure.

Although circular through holes are shown in FIGS. 5, 14, and 15, it should be appreciated that any other suitable through hole shape may be employed. For example, any of the through hole shapes may be elliptical, slot-shaped, rectangular, curved, polygonal, any combination thereof, or any other suitable shape. Of course, combinations of through holes with various shapes are also contemplated. For example, distal through holes 30*a* and 20*b* in FIG. 5 may be slot shaped, such that a dimension in the transverse direction TD may be greater than a dimension in the lateral direction LD, while proximal through holes 20*a* and 30*b* may be circular. It should be appreciated that the current disclosure is not limited by the arrangement, shape, size, orientation, and/or any combination of the aforementioned factors.

In some embodiments, a length of a device may be at least 2 cm, 2.1 cm, 2.2 cm. 2.3 cm. 2.4 cm, 2.5 cm, 2.6 cm, 2.7 cm, 2.8 cm, 2.9 cm, 3 cm, 3.5 cm, 4 cm, 4.5 cm, 5 cm, 5.5 cm, 6 cm, or any other suitable size. The length L1 of the device may also be less than or equal to 6 cm, 5.5 cm, 5 cm, 4.5 cm, 4 cm, 3.5 cm, 3 cm, 2.9 cm, 2.8 cm, 2.7 cm, 2.6 cm. 2.5 cm, 2.4 cm, 2.3 cm, 2.2 cm. 2.1 cm, 2 cm, or any other suitable size. Combinations of these ranges are also contemplated, including, for example, a device with a length L1 that is between 2 cm and 6 cm, 2 cm and 3 cm, 3 cm and 6 cm, or any other suitable range of sizes. In some embodiments, the length L1 the device may be 2.5 cm. In other embodiments, the length may be 6 cm. It should be appreciated that the length of the device may be adjusted to match a defect length when the length is parallel to the transverse direction of the defect. Accordingly, the device may be used with any defect size, ranging from 2 mm to 15 cm, or any other size, as the present disclosure is not limited by the size of the defect.

In some embodiments, a width of a device may be at least 4 mm, 4.5 mm, 5 mm, 5.5 mm, 6 mm, 6.5 mm, 7 mm, 7.5 mm, 8 mm, 10 mm, or any other suitable size. The width W1 of the device 10, 100, 1000 may also be less than or equal to 10 mm, 8 mm, 7.5 mm, 7 mm, 6.5 mm, 6 mm, 5.5 mm, 5 mm, 4.5 mm, 4 mm, or any other suitable size. Combinations of these ranges are also contemplated, including, for example, a device with a width that is between 4 mm and 10 mm, 5 mm and 8 mm, 6 mm and 10 mm, or any other suitable range of sizes. In some embodiments, the device may be delivered to the defect site through a lumen of a surgical instrument (e.g., laparoscope, endoscope, catheter, trocar). In these embodiments, the width may be less than 8 mm to allow the device to pass through the instrument. In other embodiments, the device may be placed on a defect site which may be accessible to a surgeon ("open" surgical events). In these embodiments, the device may be any suitable width to be manipulated by the surgeon.

In some embodiments, a thickness of a device may be suitably sized to allow the device to flexibly conform to the surface of the defect. In some embodiments, the defect may exist over a curved surface. Therefore, the device may be flexible enough to conform to the curved surface of the defect surface. In some embodiments, the thickness may be at least 1 mm, 1.1 mm, 1.2 mm, 1.3 mm, 1.4 mm, 1.5 mm, 1.6 mm, 1.7 mm, 1.8 mm, 1.9 mm, 2 mm, or any other suitable size. The thickness H of the device 10, 100, 1000 may also be less than or equal to 2 mm, 1.9 mm, 1.8 mm, 1.7 mm, 1.6 mm, 1.5 mm, 1.4 mm, 1.3 mm, 1.2 mm, 1.1 mm, 1 mm, or any other suitable size. Combinations of these ranges are also contemplated, including, for example, a device with a thickness that is between 1 and 2 mm, 1 and 1.5 mm, 1.2 and 2 mm, or any other suitable range of sizes.

It should be appreciated that the flexural stiffness of a device may be proportional to the cube of the thickness, regardless of the shape (e.g., rounded rectangular, elliptical, etc.) of the device. Accordingly, the thickness may be selected based on the lateral size (e.g., width W1 and length L1) of the device. For example, the thickness of a device with a large width and length may be greater than the thickness of a device with a smaller width and length. The stiffness of the device may be tuned with a combination of geometry and material properties (e.g., Young's modulus), such that the device may have a suitable stiffness for its desired application. In some embodiments, it may be desirable for the device to have a low stiffness. For example, if the device is installed on a soft but dynamic surface, it may be desirable for the device to be more flexible than if the device were installed on a rigid and static surface. Accordingly, the device is not limited to any particular thickness.

It should be appreciated that the devices disclosed herein may be used in surgical or non-surgical applications and may therefore be sized and/or shaped appropriately for the application. Accordingly, the devices described herein are not limited to any particular shape or size.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter.

The invention claimed is:

1. A surgical device for securing sutures to soft tissue, the device comprising:

an elongated body including a length and a width, wherein the length is greater than the width;

a first plurality of through holes extending from a first surface of the elongated body to a second surface of the elongated body opposite from the first surface, wherein the first plurality of through holes are positioned along at least a first portion of the length of the elongated body; and a second plurality of through holes extending from the first surface to the second surface of the elongated body, wherein the second plurality of through holes are positioned along at least a second portion of the length of the elongated body, wherein the second plurality of through holes is offset from the first plurality of through holes in a transverse direction parallel to the width of the elongated body such that the first plurality of through holes are located on a first side of a longitudinal axis of the elongated body and the second plurality of through holes are located on a second opposing side of the longitudinal axis of the elongated body, wherein the first plurality of through holes comprises each of the through holes located on the first side of the elongated body and the second plurality of through holes comprises each of the through holes located on the second side of the elongated body, wherein the first plurality of through holes are offset from the second plurality of through holes along a longitudinal direction parallel to the longitudinal axis such that each of the first plurality of through holes and each of the second plurality of through holes do not overlap with one another along the longitudinal direction, and wherein the first and second plurality of through holes are configured to receive one or more sutures to close a defect.

2. The surgical device of claim 1, wherein the first portion of the length of the elongated body and the second portion of the length of the elongated body partially overlap.

3. The surgical device of claim 1, wherein the first plurality of through holes are positioned along a first axis parallel to the longitudinal axis of the elongated body, and wherein the second plurality of through holes are positioned along a second axis parallel to the longitudinal axis of the elongated body.

4. The surgical device of claim 3, wherein a pitch of the first plurality of through holes is equal to a pitch of the second plurality of through holes.

5. The surgical device of claim 3, wherein the first plurality of through holes positioned along the first axis are offset from the second plurality of through holes positioned along the second axis such that the first plurality of through holes are not aligned with the second plurality of through holes along an axis parallel to the transverse direction.

6. The surgical device of claim 1, wherein the first plurality of through holes and the second plurality of through holes are offset by at least 6 mm in the transverse direction.

7. The surgical device of claim 1, wherein the width is less than 8 mm.

8. The surgical device of claim 1, wherein the first plurality of through holes and the second plurality of through holes are circular.

9. The surgical device of claim 1, wherein the device is formed of a bioresorbable material.

10. The surgical device of claim 1, wherein the first plurality of through holes includes at least two through holes, and wherein the second plurality of through holes includes at least two through holes.

11. A surgical device for securing sutures to soft tissue, the device comprising:

an elongated body including a length and a width, wherein the length is greater than the width;

a marker located along a portion of the elongated body, the marker being constructed and arranged to be visually distinct from a remainder of the elongated body as a result of having one or more distinct optical properties selected from the group of a different color, a different opacity, a different material, and a groove extending along at least a portion of the width of the elongated body;

a first plurality of through holes extending from a first surface of the elongated body to a second surface of the elongated body opposite from the first surface, wherein the first plurality of through holes are positioned along at least a first portion of the length of the elongated body; and a second plurality of through holes extending from the first surface to the second surface of the elongated body, wherein the second plurality of through holes are positioned along at least a second portion of the length of the elongated body, wherein the second plurality of through holes is offset from the first plurality of through holes in a transverse direction parallel to the width of the elongated body, wherein the first and second plurality of through holes are configured to receive one or more sutures to close a defect.

12. The surgical device of claim 11, wherein the marker is located at a midline of the elongated body.

13. The surgical device of claim 11, wherein the marker includes the groove extending along at least the portion of the width of the elongated body.

14. The surgical device of claim 11, wherein the first plurality of through holes are positioned along a first axis parallel to a longitudinal axis of the elongated body, and wherein the second plurality of through holes are positioned along a second axis parallel to the longitudinal axis of the elongated body.

15. The surgical device of claim 14, wherein the first plurality of through holes positioned along the first axis are offset from the second plurality of through holes positioned along the second axis such that the first plurality of through holes are not aligned with the second plurality of through holes along an axis parallel to the transverse direction.

16. The surgical device of claim 14, wherein a pitch of the first plurality of through holes is equal to a pitch of the second plurality of through holes.

* * * * *